(12) United States Patent
Goff et al.

(10) Patent No.: US 12,233,214 B2
(45) Date of Patent: *Feb. 25, 2025

(54) PORTABLE PAP DEVICE WITH HUMIDIFICATION

(71) Applicant: ResMed Inc., San Diego, CA (US)

(72) Inventors: Thomas G. Goff, Mountain View, CA (US); Kirby Chiang, Mountain View, CA (US); Nathaniel Bowditch, Menlo Park, CA (US)

(73) Assignee: ResMed Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,046

(22) Filed: Sep. 28, 2023

(65) Prior Publication Data
US 2024/0139461 A1 May 2, 2024

Related U.S. Application Data

(63) Continuation of application No. 17/111,927, filed on Dec. 4, 2020, now Pat. No. 11,813,385, which is a
(Continued)

(51) Int. Cl.
*A61M 16/16* (2006.01)
*A61M 11/00* (2006.01)
(Continued)

(52) U.S. Cl.
CPC .......... *A61M 16/16* (2013.01); *A61M 11/005* (2013.01); *A61M 16/0057* (2013.01);
(Continued)

(58) Field of Classification Search
CPC ............ A61M 11/005; A61M 16/0816; A61M 16/1095; A61M 16/0808; A61M 16/162;
(Continued)

(56) References Cited

U.S. PATENT DOCUMENTS

| | | |
|---|---|---|
| 3,649,964 A | 3/1972 | Schoelz et al. |
| 3,721,233 A | 3/1973 | Montgomery et al. |

(Continued)

FOREIGN PATENT DOCUMENTS

| | | |
|---|---|---|
| CN | 101678220 A | 3/2010 |
| FR | 2853838 A1 | 10/2004 |

(Continued)

OTHER PUBLICATIONS

Cartwright; Effect of sleep position on sleep apnea severity; Sleep;7(2); pp. 110-114; Jun. 1984.
(Continued)

*Primary Examiner* — Colin W Stuart
*Assistant Examiner* — Douglas Y Sul
(74) *Attorney, Agent, or Firm* — Botos Churchill IP Law LLP

(57) ABSTRACT

A portable, efficient, integrated humidification system for use, e.g., with a positive airway pressure devices. The portable, efficient, integrated humidification system described herein offers many advantages over current humidification systems! There are many advantages to a portable respiratory humidifier. Portability reduces the amount of space the humidifier occupies in the user's bedroom environment. Portability enhances travel for the user. With less to pack, carry, and manage, the user is more likely to remain adherent to therapy when not at home. Portability allows for better utilization in recreational vehicles, while camping, in foreign countries, in the sleeping cabins of trucks or airliners, and on marine craft.

23 Claims, 15 Drawing Sheets

Related U.S. Application Data continuation of application No. 15/329,150, filed as application No. PCT/US2015/044416 on Aug. 10, 2015, now Pat. No. 10,881,829.

(60) Provisional application No. 62/038,781, filed on Aug. 18, 2014.

(51) Int. Cl.
   *A61M 16/00* (2006.01)
   *A61M 16/08* (2006.01)
   *A61M 16/10* (2006.01)

(52) U.S. Cl.
   CPC .... *A61M 16/0808* (2013.01); *A61M 16/0816* (2013.01); *A61M 16/109* (2014.02); *A61M 16/1095* (2014.02); *A61M 16/162* (2013.01); *A61M 2016/0021* (2013.01); *A61M 2016/0027* (2013.01); *A61M 2016/003* (2013.01); *A61M 2016/0039* (2013.01); *A61M 2205/3368* (2013.01); *A61M 2205/3379* (2013.01); *A61M 2205/75* (2013.01); *A61M 2205/7545* (2013.01)

(58) Field of Classification Search
   CPC .............. A61M 16/16; A61M 2205/75; A61M 2205/3379
   See application file for complete search history.

(56) References Cited

U.S. PATENT DOCUMENTS

| | | | |
|---|---|---|---|
| 3,736,927 A | 6/1973 | Misaqi | |
| 3,821,947 A | 7/1974 | Schossow | |
| 3,822,698 A | 7/1974 | Guy | |
| 3,881,198 A | 5/1975 | Waters | |
| 3,998,213 A | 12/1976 | Price | |
| 4,019,508 A | 4/1977 | Der et al. | |
| 4,037,595 A | 7/1977 | Elam | |
| 4,206,644 A | 6/1980 | Platt | |
| 4,233,972 A | 11/1980 | Hauff et al. | |
| 4,297,999 A | 11/1981 | Kitrell | |
| 4,381,267 A | 4/1983 | Jackson | |
| 4,425,501 A | 1/1984 | Stauffer | |
| 4,430,995 A | 2/1984 | Hilton | |
| 4,456,179 A * | 6/1984 | Kremer | B05B 7/0012 239/338 |
| 4,549,542 A | 10/1985 | Chien | |
| 4,588,425 A | 5/1986 | Usry et al. | |
| 4,590,951 A | 5/1986 | O'Connor | |
| 4,644,947 A | 2/1987 | Whitwam et al. | |
| 4,765,316 A | 8/1988 | Marshall | |
| 4,782,832 A | 11/1988 | Trimble et al. | |
| 4,802,485 A | 2/1989 | Bowers et al. | |
| 4,829,998 A | 5/1989 | Jackson | |
| 4,836,219 A | 6/1989 | Hobson et al. | |
| 4,944,310 A | 7/1990 | Sullivan | |
| 5,035,239 A | 7/1991 | Edwards | |
| 5,046,492 A | 9/1991 | Stackhouse et al. | |
| 5,054,480 A | 10/1991 | Bare et al. | |
| 5,054,484 A | 10/1991 | Hebeler | |
| 5,104,430 A | 4/1992 | Her-Mou | |
| 5,113,853 A | 5/1992 | Dickey | |
| 5,154,168 A | 10/1992 | Schlobohm | |
| 5,273,036 A | 12/1993 | Kronberg et al. | |
| 5,284,160 A | 2/1994 | Dryden | |
| 5,303,701 A | 4/1994 | Heins et al. | |
| 5,318,020 A | 6/1994 | Schegerin | |
| 5,349,946 A | 9/1994 | McComb | |
| 5,353,788 A | 10/1994 | Miles | |
| 5,372,130 A | 12/1994 | Stern et al. | |
| 5,377,670 A | 1/1995 | Smith | |
| 5,394,870 A | 3/1995 | Johansson | |
| 5,443,059 A * | 8/1995 | Koch | A61M 16/147 128/204.23 |
| 5,461,934 A | 10/1995 | Budd | |
| 5,485,851 A | 1/1996 | Erickson | |
| 5,501,212 A | 3/1996 | Psaros | |
| 5,517,986 A | 5/1996 | Starr et al. | |
| 5,533,500 A | 7/1996 | Her-Mou | |
| RE35,339 E | 10/1996 | Rapoport | |
| 5,564,124 A | 10/1996 | Elsherif et al. | |
| 5,577,496 A | 11/1996 | Blackwood et al. | |
| 5,584,296 A | 12/1996 | Cui et al. | |
| 5,649,533 A | 7/1997 | Oren | |
| 5,657,752 A | 8/1997 | Landis et al. | |
| 5,769,071 A | 6/1998 | Turnbull | |
| 5,928,189 A | 7/1999 | Phillips et al. | |
| 5,937,855 A | 8/1999 | Zdrojkowski et al. | |
| 5,950,621 A | 9/1999 | Klockseth et al. | |
| 5,954,050 A | 9/1999 | Christopher | |
| 5,961,447 A | 10/1999 | Raviv | |
| D421,298 S | 2/2000 | Kenyon et al. | |
| 6,050,262 A | 4/2000 | Jay | |
| 6,078,730 A | 6/2000 | Huddart et al. | |
| 6,095,505 A | 8/2000 | Miller | |
| 6,122,773 A | 9/2000 | Katz | |
| 6,135,106 A | 10/2000 | Dirks et al. | |
| 6,179,586 B1 | 1/2001 | Herb et al. | |
| 6,213,119 B1 | 4/2001 | Brydon et al. | |
| 6,349,724 B1 | 2/2002 | Burton et al. | |
| 6,367,474 B1 | 4/2002 | Berthon-Jones et al. | |
| 6,371,112 B1 | 4/2002 | Bibi | |
| 6,393,617 B1 | 5/2002 | Paris et al. | |
| 6,397,845 B1 | 6/2002 | Burton | |
| 6,431,171 B1 | 8/2002 | Burton | |
| 6,435,180 B1 | 8/2002 | Hewson et al. | |
| 6,435,184 B1 | 8/2002 | Ho | |
| 6,470,887 B1 | 10/2002 | Martinez | |
| 6,513,526 B2 | 2/2003 | Kwok | |
| 6,532,960 B1 | 3/2003 | Yurko | |
| 6,561,190 B1 | 5/2003 | Kwok | |
| 6,561,191 B1 | 5/2003 | Kwok | |
| 6,615,831 B1 | 9/2003 | Tuitt et al. | |
| 6,622,311 B2 | 9/2003 | Diaz et al. | |
| 6,622,726 B1 | 9/2003 | Du | |
| 6,626,174 B1 | 9/2003 | Genger et al. | |
| 6,634,864 B1 | 10/2003 | Young et al. | |
| 6,694,978 B1 | 2/2004 | Bennarsten | |
| 6,705,314 B1 | 3/2004 | Odea | |
| 6,708,050 B2 | 3/2004 | Carim | |
| 6,709,405 B2 | 3/2004 | Jonson | |
| 6,730,927 B1 | 5/2004 | Smith et al. | |
| 6,733,556 B1 | 5/2004 | Delvigo | |
| 6,752,146 B1 | 6/2004 | Altshuler et al. | |
| 6,772,760 B2 | 8/2004 | Frater et al. | |
| 6,772,762 B2 | 8/2004 | Piesinger | |
| 6,793,629 B2 | 9/2004 | Rapoport et al. | |
| 6,854,465 B2 | 2/2005 | Bordewick et al. | |
| 6,881,192 B1 | 4/2005 | Park | |
| 6,889,691 B2 | 5/2005 | Eklund et al. | |
| 6,895,959 B2 | 5/2005 | Lukas | |
| 6,895,962 B2 | 5/2005 | Kullik et al. | |
| 6,918,389 B2 | 7/2005 | Seakins et al. | |
| 6,920,877 B2 | 7/2005 | Remmers et al. | |
| 6,932,084 B2 | 8/2005 | Estes et al. | |
| 6,973,929 B2 | 12/2005 | Gunaratnam | |
| 6,990,980 B2 | 1/2006 | Richey, II | |
| 7,019,652 B2 | 3/2006 | Richardson | |
| 7,069,932 B2 | 7/2006 | Eaton et al. | |
| 7,086,422 B2 | 8/2006 | Huber et al. | |
| 7,089,941 B2 | 8/2006 | Bordewick et al. | |
| 7,096,864 B1 | 8/2006 | Mayer et al. | |
| 7,118,608 B2 | 10/2006 | Lovell | |
| 7,156,090 B2 | 1/2007 | Nomori | |
| 7,178,525 B2 | 2/2007 | Matula et al. | |
| 7,195,014 B2 | 3/2007 | Hoffman | |
| 7,200,873 B2 | 4/2007 | Klotz et al. | |
| 7,204,250 B1 | 4/2007 | Burton | |
| 7,255,103 B2 | 8/2007 | Bassin | |
| 7,285,090 B2 | 10/2007 | Stivoric et al. | |
| 7,297,119 B2 | 11/2007 | Westbrook et al. | |

(56) References Cited

U.S. PATENT DOCUMENTS

| | | | |
|---|---|---|---|
| 7,357,136 B2 | 4/2008 | Ho et al. |
| D570,473 S | 6/2008 | Hamaguchi et al. |
| 7,382,247 B2 | 6/2008 | Welch et al. |
| 7,406,966 B2 | 8/2008 | Wondka |
| 7,406,996 B2 | 8/2008 | Schuh |
| 7,471,290 B2 | 12/2008 | Wang et al. |
| 7,478,635 B2 | 1/2009 | Wixey et al. |
| 7,487,778 B2 | 2/2009 | Freitag |
| 7,516,743 B2 | 4/2009 | Hoffman |
| 7,575,005 B2 | 8/2009 | Mumford et al. |
| 7,588,033 B2 | 9/2009 | Wondka |
| 7,664,546 B2 | 2/2010 | Hartley et al. |
| 7,681,575 B2 | 3/2010 | Wixey et al. |
| 7,738,935 B1 | 6/2010 | Turcott |
| 7,766,841 B2 | 8/2010 | Yamamoto et al. |
| 7,862,521 B1 | 1/2011 | Kodama et al. |
| 7,887,492 B1 | 2/2011 | Rulkov et al. |
| 7,913,692 B2 | 3/2011 | Kwok |
| 7,934,500 B2 | 5/2011 | Madaus et al. |
| 7,942,824 B1 | 5/2011 | Kayyali et al. |
| 7,975,687 B2 | 7/2011 | Gruendler et al. |
| D643,929 S | 8/2011 | Dellostritto et al. |
| 8,020,557 B2 | 9/2011 | Bordewick et al. |
| 8,061,354 B2 | 11/2011 | Schneider et al. |
| 8,135,377 B2 | 3/2012 | Baghdasaryan |
| D659,235 S | 5/2012 | Bertinetti et al. |
| 8,172,766 B1 | 5/2012 | Kayyali et al. |
| 8,316,848 B2 | 11/2012 | Kwok et al. |
| 8,327,846 B2 | 12/2012 | Bowditch et al. |
| 8,336,546 B2 | 12/2012 | Bowditch et al. |
| 8,353,290 B2 | 1/2013 | Adams |
| D683,444 S | 5/2013 | Inoue et al. |
| D683,445 S | 5/2013 | Inoue |
| 8,453,640 B2 | 6/2013 | Martin et al. |
| 8,453,681 B2 | 6/2013 | Forrester et al. |
| 8,475,370 B2 | 7/2013 | McCombie et al. |
| 8,517,017 B2 | 8/2013 | Bowditch et al. |
| 8,591,430 B2 | 11/2013 | Amurthur et al. |
| D696,393 S | 12/2013 | Lu |
| D696,394 S | 12/2013 | Lu |
| 8,688,187 B2 | 4/2014 | Dellostritto et al. |
| 8,720,439 B1 | 5/2014 | Kolkowski et al. |
| 8,733,349 B2 | 5/2014 | Bath et al. |
| 8,740,806 B2 | 6/2014 | Parfenova et al. |
| 8,880,207 B2 | 11/2014 | Abeyratne et al. |
| 8,903,467 B2 | 12/2014 | Sweitzer et al. |
| 8,919,344 B2 | 12/2014 | Bowditch et al. |
| 8,925,546 B2 | 1/2015 | Bowditch et al. |
| D732,158 S | 6/2015 | Salmon et al. |
| D734,446 S | 7/2015 | Salmon et al. |
| D740,929 S | 10/2015 | Pipe et al. |
| D740,930 S | 10/2015 | Pipe et al. |
| 9,180,267 B2 | 11/2015 | Bowditch et al. |
| 9,216,264 B2 | 12/2015 | Ho |
| D776,802 S | 1/2017 | Loew et al. |
| 9,833,591 B1 | 12/2017 | Ormrod |
| 10,881,829 B2 * | 1/2021 | Goff ............... A61M 16/0816 |
| 2002/0078958 A1 | 6/2002 | Stenzler |
| 2002/0104541 A1 | 8/2002 | Bibi et al. |
| 2003/0062045 A1 | 4/2003 | Woodring et al. |
| 2003/0079749 A1 | 5/2003 | Strickland et al. |
| 2004/0079373 A1 | 4/2004 | Mukaiyama et al. |
| 2004/0163648 A1 | 8/2004 | Burton |
| 2004/0186681 A1 | 9/2004 | Harle |
| 2004/0226562 A1 | 11/2004 | Bordewick |
| 2004/0254524 A1 | 12/2004 | Spearman et al. |
| 2005/0005937 A1 | 1/2005 | Farrugia et al. |
| 2005/0028811 A1 | 2/2005 | Nelson et al. |
| 2005/0034724 A1 | 2/2005 | O'Dea |
| 2005/0068639 A1 | 3/2005 | Pierrat et al. |
| 2005/0131288 A1 | 6/2005 | Turner et al. |
| 2005/0133039 A1 | 6/2005 | Wood |
| 2005/0188991 A1 | 9/2005 | Sun et al. |
| 2006/0037613 A1 | 2/2006 | Kwok et al. |
| 2006/0081250 A1 | 4/2006 | Bordewick et al. |
| 2006/0096596 A1 | 5/2006 | Occhialini et al. |
| 2006/0150973 A1 | 7/2006 | Chalvignac |
| 2006/0150978 A1 | 7/2006 | Doshi et al. |
| 2006/0173257 A1 | 8/2006 | Nagai et al. |
| 2006/0180149 A1 | 8/2006 | Matarasso |
| 2006/0231097 A1 | 10/2006 | Dougherty et al. |
| 2006/0249149 A1 | 11/2006 | Meier et al. |
| 2007/0000493 A1 | 1/2007 | Cox |
| 2007/0113854 A1 | 5/2007 | McAuliffe |
| 2007/0163592 A1 | 7/2007 | Reinstadtler et al. |
| 2007/0169781 A1 | 7/2007 | Tang |
| 2007/0208269 A1 | 9/2007 | Mumford et al. |
| 2007/0221220 A1 | 9/2007 | Bright |
| 2007/0240716 A1 | 10/2007 | Marx |
| 2007/0247009 A1 | 10/2007 | Hoffman et al. |
| 2007/0251527 A1 | 11/2007 | Sleeper |
| 2007/0277825 A1 | 12/2007 | Bordewick et al. |
| 2008/0006275 A1 | 1/2008 | Nickelson et al. |
| 2008/0053451 A1 | 3/2008 | Bordewick et al. |
| 2008/0060649 A1 | 3/2008 | Veliss et al. |
| 2008/0078382 A1 | 4/2008 | Lemahieu et al. |
| 2008/0091090 A1 | 4/2008 | Guillory et al. |
| 2008/0127976 A1 | 6/2008 | Acker |
| 2008/0147147 A1 | 6/2008 | Griffiths et al. |
| 2008/0149101 A1 | 6/2008 | Becker et al. |
| 2008/0178879 A1 | 7/2008 | Roberts et al. |
| 2008/0185002 A1 | 8/2008 | Berthon-Jones et al. |
| 2008/0200786 A1 | 8/2008 | Berndsen |
| 2008/0202527 A1 | 8/2008 | Hutchinson et al. |
| 2008/0216831 A1 | 9/2008 | McGinnis et al. |
| 2008/0251079 A1 | 10/2008 | Richey |
| 2008/0304986 A1 | 12/2008 | Kenyon et al. |
| 2009/0044810 A1 | 2/2009 | Kwok et al. |
| 2009/0065005 A1 | 3/2009 | Ades |
| 2009/0078255 A1 | 3/2009 | Bowman et al. |
| 2009/0078258 A1 | 3/2009 | Bowman et al. |
| 2009/0078259 A1 | 3/2009 | Kooij et al. |
| 2009/0194101 A1 | 8/2009 | Kenyon et al. |
| 2009/0241948 A1 * | 10/2009 | Clancy ............... A61M 15/0085 128/203.14 |
| 2009/0267242 A1 | 10/2009 | Nichols et al. |
| 2009/0326353 A1 | 12/2009 | Watson et al. |
| 2010/0024811 A1 | 2/2010 | Henry et al. |
| 2010/0083965 A1 | 4/2010 | Virr et al. |
| 2010/0139661 A1 | 6/2010 | Landis |
| 2010/0180895 A1 | 7/2010 | Kwok et al. |
| 2010/0186745 A1 | 7/2010 | Mashak |
| 2010/0191076 A1 | 7/2010 | Lewicke et al. |
| 2010/0206308 A1 | 8/2010 | Klasek et al. |
| 2010/0229867 A1 | 9/2010 | Bertinetti et al. |
| 2010/0240982 A1 | 9/2010 | Westbrook et al. |
| 2010/0312513 A1 | 12/2010 | Mayor et al. |
| 2010/0319687 A1 | 12/2010 | Esaki et al. |
| 2011/0046462 A1 | 2/2011 | Ono et al. |
| 2011/0056489 A1 | 3/2011 | Slaker et al. |
| 2011/0100366 A1 | 5/2011 | Chou |
| 2011/0105915 A1 | 5/2011 | Bauer |
| 2011/0108031 A1 | 5/2011 | Wilday et al. |
| 2011/0192400 A9 | 8/2011 | Burton |
| 2011/0218409 A1 | 9/2011 | Kugler et al. |
| 2011/0295083 A1 | 12/2011 | Doelling et al. |
| 2012/0016219 A1 | 1/2012 | Fujii |
| 2012/0097156 A1 | 4/2012 | Bowman et al. |
| 2012/0108928 A1 | 5/2012 | Tverskoy |
| 2012/0125334 A1 * | 5/2012 | Korneff ............... A61M 11/005 128/203.26 |
| 2012/0138050 A1 | 6/2012 | Wondka et al. |
| 2012/0146251 A1 | 6/2012 | Heine et al. |
| 2012/0152239 A1 | 6/2012 | Shikani et al. |
| 2012/0152255 A1 | 6/2012 | Barlow et al. |
| 2012/0167879 A1 | 7/2012 | Bowman |
| 2012/0174916 A1 | 7/2012 | Kern |
| 2012/0179005 A1 | 7/2012 | McCool |
| 2012/0266873 A1 | 10/2012 | Lalonde |
| 2012/0298099 A1 | 11/2012 | Lalonde |
| 2012/0304985 A1 | 12/2012 | Lalonde |
| 2013/0060098 A1 | 3/2013 | Thomsen et al. |
| 2013/0081701 A1 | 4/2013 | Korneff et al. |
| 2013/0104883 A1 | 5/2013 | Lalonde |

(56) References Cited

U.S. PATENT DOCUMENTS

| | | |
|---|---|---|
| 2013/0146054 A1 | 6/2013 | Ho |
| 2013/0239966 A1 | 9/2013 | Heidmann et al. |
| 2013/0263845 A1* | 10/2013 | Arcilla ............... A61M 16/142 |
| | | 128/200.14 |
| 2013/0298908 A1 | 11/2013 | Tang et al. |
| 2013/0306074 A1 | 11/2013 | Bowditch et al. |
| 2013/0333701 A1 | 12/2013 | Herron |
| 2014/0000600 A1 | 1/2014 | Dimatteo et al. |
| 2014/0007881 A1 | 1/2014 | Rummery et al. |
| 2014/0053939 A1 | 2/2014 | Kaye et al. |
| 2014/0090649 A1 | 4/2014 | Groll et al. |
| 2014/0102456 A1 | 4/2014 | Ovizinsky et al. |
| 2014/0127996 A1 | 5/2014 | Park et al. |
| 2014/0144445 A1 | 5/2014 | Bowditch et al. |
| 2014/0158128 A1* | 6/2014 | Heimel ............... A61M 16/109 |
| | | 128/203.29 |
| 2014/0191054 A1* | 7/2014 | Hingley ............... G01F 23/241 |
| | | 239/74 |
| 2014/0236083 A1 | 8/2014 | Sims |
| 2015/0040908 A1 | 2/2015 | Goff et al. |
| 2015/0083136 A1 | 3/2015 | Grashow et al. |
| 2015/0094552 A1 | 4/2015 | Golda et al. |
| 2015/0173672 A1 | 6/2015 | Goldstein |
| 2015/0197378 A1 | 7/2015 | Miller et al. |
| 2015/0217074 A1 | 8/2015 | Wells et al. |
| 2015/0352299 A1 | 12/2015 | Cortez et al. |
| 2015/0367092 A1 | 12/2015 | Goff et al. |
| 2016/0015916 A1 | 1/2016 | Goff et al. |
| 2017/0143931 A1* | 5/2017 | Zheng ............... A61M 16/164 |

FOREIGN PATENT DOCUMENTS

| | | |
|---|---|---|
| WO | 9119527 A1 | 12/1991 |
| WO | 9913931 A1 | 3/1999 |
| WO | 9921602 A1 | 5/1999 |
| WO | 02085417 A2 | 10/2002 |
| WO | 2007149446 A2 | 12/2007 |
| WO | 2008028247 A1 | 3/2008 |
| WO | 2009124076 A1 | 10/2009 |
| WO | 2010107913 A2 | 9/2010 |
| WO | 2011127385 A1 | 10/2011 |
| WO | 2014210588 A1 | 12/2014 |

OTHER PUBLICATIONS

Colrain et al.; The use of a nasal resistance valve to treat sleep disordered breathing (Abstract No. 0518); Sleep 2008 22nd Ann. Mtg. Assoc. Prof. Sleep Soc., LLC; Baltimore, MD; vol. 31, Abstract Suppl.; p. A172; Jun. 7-12, 2008.

Goff et al.; U.S. Appl. No. 15/551,671 entitled "Hose for respiratory device," filed Aug. 17, 2017.

Goff et al.; U.S. Appl. No. 16/195,624 entitled "Positional obstructive sleep apnea detection system," filed Nov. 19, 2018.

Gunaratnam et al.; U.S. Appl. No. 60/494,119 entitled "Nasal Assembly," filed Aug. 12, 2003 (119 pgs.).

H0fsoy et al.; Monitoring and therapy of sleep related breathing disorders; IEEE; 6th Ann. Workshop on Wearable Micro and Nano Technologies for Personalized Heath (pHealth); pp. 41-44; Jun. 24-26, 2009.

Kwok, Philip R.; U.S. Appl. No. 60/505,718 entitled "Ventilator mask and system," filed Sep. 25, 2003 (37 pgs.).

Oksenberg et al.; Association of body position with severity of apneic events in patients with severe non-positional obstructive sleep apnea; Chest; 118(4); pp. 1018-1024; Oct. 2000.

Penzel et al.; Effect of sleep position and sleep stage on the collapsibility of the upper airways in patients with sleep apnea; Sleep; 24(1); pp. 90-95; Feb. 2001.

Pevernagie et al.; Relations between sleep stage, posture and effective nasal CPAP levels in OSA; Sleep; 15(2); pp. 162-167; Apr. 1992.

Massie, et al., Acceptance and adherence of a novel device in the treatment of mild to moderate obstructive sleep apnea (Abstract No. 0644); Sleep 2008 22nd Ann. Mtg. Assoc. Prof. Sleep Soc., LLC; Baltimore, MD; vol. 31, Abstract Suppl.; p. A211; Jun. 7-12, 2008.

* cited by examiner

PORTABLE PAP DEVICE WITH HUMIDIFICATION

CROSS-REFERENCE TO RELATED APPLICATIONS

This application is a continuation of U.S. patent application Ser. No. 17/111,927, filed Dec. 4, 2020, which is a continuation of U.S. patent application Ser. No. 15/329,150, filed Jan. 25, 2017, which is a national phase entry under 35 U.S.C. § 371 of International Application No. PCT/US2015/44416 filed Aug. 10, 2015, published in English, which claims priority from U.S. Provisional Patent Application No. 62/038,781, filed Aug. 18, 2014, all of which are incorporated herein by reference.

All publications and patent applications mentioned in this specification are herein incorporated by reference in their entirety to the same extent as if each individual publication or patent application was specifically and individually indicated to be incorporated by reference.

BACKGROUND OF THE INVENTION

Obstructive sleep apnea (OSA) occurs when tissue in the upper airway blocks the airway during sleep. The brain will sense the rise in CO2, and will wake up the person so that breathing resumes. Such an event is called an apnea. A partial airway blockage causing an awakening is called a hypopnea. A person is unlikely to remember such awakenings, but sleep is disrupted. The severity of obstructive sleep apnea is measured by the frequency of awakenings, as shown in the table below.

| Apneas + Hypopneas/Hour | OSA Classification |
|---|---|
| 0-5 | Normal |
| 5-15 | Mild |
| 15-30 | Moderate |
| 30+ | Severe |

Untreated, OSA not only leaves patients chronically fatigued, but it also carries significant cardiovascular consequences.

Positive Airway Pressure, or PAP, is the most widely used and the most effective treatment for OSA. In PAP, a bedside compressor supplies pressurized air to the patient's airway through a hose and mask. The air pressure is set sufficiently high to maintain an open airway during sleep. Examples of PAP devices may be found, e.g., in U.S. Pat. Nos. 8,316,848; 8,453,640; and 8,353,290, the disclosures of which are incorporated herein by reference.

Many OSA patients who use PAP have difficulty using their PAP systems when traveling. Most PAP systems are both bulky and too fragile to pack in checked luggage. For travel, patients prefer small, light PAP systems. Despite recent introduction of some portable PAP systems, there remain significant shortcomings in their design.

Smaller, more travel-friendly PAP machines are being introduced to the market. However, they either lack humidification or, if they include it, it requires extra bulk.

Many travelers leave their humidification systems at home when they travel. The humidification units for many PAP systems are just as large as the flow generator. Humidification units are comprised of a large reservoir for holding water, and technology to convert the fluid water into a mist or vapor. The bulk of the water chamber is not compressible, and therefore inhibits portability and travel.

Standard humidification systems for positive airway pressure devices typically comprise a heated water reservoir and a flow path for the PAP airflow to pass over the heated water, thereby becoming humidified. These systems have several shortcomings. Among the shortcomings are size and power requirements. Bulky systems take up valuable personal space and are less portable for travel. These systems also have higher power requirements, as they must maintain a large mass of water at a heated temperature during the entire use. This results in a less efficient, bulkier system. Further, these systems require daily maintenance and cleaning. Some are also prone to spilling. Spilling water in the bedroom environment, near electronics, electrical power, and personal items, can be a significant problem and dissuade humidifier use.

BRIEF SUMMARY OF THE INVENTION

The portable, efficient, integrated humidification system described herein offers many advantages over current humidification systems.

There are many advantages to a portable respiratory humidifier. Portability reduces the amount of space the humidifier occupies in the user's bedroom environment. Portability enhances travel for the user. With less to pack, carry, and manage, the user is more likely to remain adherent to therapy when not at home. Portability allows for better utilization in recreational vehicles, while camping, in foreign countries, in the sleeping cabins of trucks or airliners, and on marine craft.

For the humidification system, a fluid source is required. In most cases this is in the form of a water reservoir. Classic humidification systems incorporate a tank for holding the fluid. These tanks typically hold 300-500 mL or more. Travel with such a bulky tank is burdensome.

Another limitation of many existing humidification systems is the recommendation that distilled water be used. This is due to the evaporative designs used and the buildup of minerals left behind. In ultrasonic humidifiers, there is a concern that minerals in the water can be aerosolized and inhaled into the lungs of the user.

In all humidification systems, there are concerns of microbial organisms in the water, especially if the water reservoir and path are not consistently emptied and cleaned. Many users do not clean their devices as frequently or thoroughly as recommended by the manufacturer.

For these reasons, the incorporation of filtration and sterilization capabilities into the system may be desired.

In one embodiment of the invention, the micro-humidifier is integrated into the PAP base unit.

In another embodiment of the invention, the micro humidifier is an attachment unit that can be connected to any PAP machine to provide humidity to the airflow. This connection could occur through the standard tubing fittings. These fittings are commonly 22 mm in diameter. The connection could also be made using adaptors. The humidification unit can work using several different mechanisms well known in the art, including: evaporation, steam, ultrasonic, diffuser.

The unit can be powered through a standard wall plug or with batteries.

In a further embodiment, the humidification unit to which the bottle is attached can deliver its humidified air through a small tube that is connected to the tubing or mask interface near the patient to humidify the air.

The bottle could be connected to sit upright, upside down, or lay on its side. It could have a tube extending into it for the sourcing of the water. Bottles of various sizes could be used with the same standardized fitting. The bottle and device could also be fashioned to conveniently attach to the sleeping environment. They could attach to the headboard, sideboards, mattress, under the bed, side table, lamp or other attachments surfaces.

In a further embodiment of the invention, the humidification apparatus can also heat the water, providing heated humidification.

Another aspect of this invention is a humidification system that overcomes the shortcomings of the existing conventional systems. This is achieved according to one embodiment of the invention by providing a small, lightweight, and energy efficient humidification element in-line with the airflow tubing. This integrated hose humidifier can be part of the hose tubing, either in section or full length. The humidification element is fed from a separate connected reservoir of fluid. This fluid reservoir can be integrated with the hose humidifier. Alternatively, the fluid reservoir can be housed separately from the humidification hose. Fluid passes from the reservoir through small tubing to the humidification hose, where a humidification element transforms the fluid into vapor within the air path of the tube, where it is then carried by the flow to the user.

Several key advantages are offered by such a system. Many advantages are particularly well suited to the goals of portability and ease of use.

Separating the fluid reservoir from the humidification element offers many unique advantages. For example, the fluid reservoir can be replaced with a new one when empty. As described in more detail below, the fluid reservoir can take the form of a standard screw-top water bottle, commonly available worldwide. Further, the ability to discard and replace the fluid reservoir reduces the cleaning and maintenance burden on the user.

A fluid reservoir that is independent of the humidification element also reduces or eliminates leaks and spillage. As the reservoir can be completely enclosed, and does not depend on the ability to allow air to pass above the water to get humidified, it does not have the inherent tendency to leak that conventional systems have. Additionally, in many embodiments it is not dependent on one certain orientation with respect to gravity to work properly. This offers a significant advantage. Conventional humidification systems require that the system be maintained upright. This results in bulky systems to ensure they do not tip over from movement during use. One of the challenges of producing a compact humidification system is the requirement of conventional humidifiers to be anchored with an upright orientation. As device size is reduced, the tendency to tip and spill is increased. The invention described herein allows the independent reservoir to be placed in many different positions that still provide for successful transfer of water from the reservoir to the humidification element. Likewise the humidification element does not require a certain orientation with respect to gravity in order to work properly.

Since the humidification is integrated into the airflow hose, it allows full, unencumbered movement of the tubing during use. Conventional humidification systems do not enable movement of the hose during use. They effectively create a new, stationary base to which the tubing attaches. They are not designed to move with the tubing.

The ability to integrate the humidification directly into the tubing also allows for the humidification to occur at any point along the tubing between the flow generator and the user. Placing the humidification closer to the user offers many benefits. The humidification has less area in which to condense and cause rain out, therefore more of the humidification will reach the end user instead of lining the interior of the flow path. The ability to place the humidification element anywhere along the tubing allows for various combinations of heating before, during or after the humidification of the airflow. The compact and lightweight humidification elements described herein enable this advantage.

Further, for applications where the flow generator may be worn on the body or suspended near the user, it is significantly advantageous to separate the fluid reservoir from the humidification. It is not desired to wear 300-500 cc of water on the body throughout the night. This system allows the reservoir to be contained separately, and just the tubing with integrated humidification element to be worn by the user.

Conventional humidification systems incorporate a tank for holding 300-500 mL of fluid. A significant improvement employed by the invention is the ability to use standard threaded water bottles or similar containers as the water reservoir. Most water bottles have a standard thread opening (such as SPI 28MM thread specs). The fitting can be designed to fit the majority of flat water bottles in the marketplace. Multiple adaptors can be offered to allow for pressurized bottles, non-pressurized bottles, and bottles of varying threads available internationally. In addition to the ability to work with almost any water bottle available, water reservoirs custom designed for the application can be provided with the same threaded opening to allow for attachment. The custom reservoir could be used in a home environment, or other situations when a more repeatable, robust reservoir is desired. When traveling, a disposable water bottle can be used as the reservoir. This liberates the user from having to bring a reservoir with them—they simply procure a water bottle wherever they are, use it, and can leave it behind when they are done with it. This significantly reduces the amount of material with which a user must travel.

In another embodiment, the fluid reservoir is comprised of a collapsible reservoir. This collapsible reservoir could be in the form of a bottle made of a flexible material and folding design which can accordion into a small volume for transport, and expand into a full size reservoir for use. This enables portability for travel and expandability during use. One such design fulfilling this goal is a reservoir with preformed folds in the walls and made of an elastomer which can easily expand and collapse.

A further unique advantage of the system of this invention is the efficiency with which the fluid is aerosolized into the air path. In one embodiment, an ultrasonic nebulizer creates vaporized droplets of water with low energy demand. A further embodiment allows for the selective activation of the system. Conventional humidification systems are always on or always off. The system described herein can be cycled on and off rapidly. This can be timed with the respiratory cycle, thereby providing humidified air during inspiration, but not during expiration. This reduces the unnecessary waste of energy and water, and can reduce the incidence of "rain out," a common annoyance for users wherein humidification condenses in the circuit and water droplets run onto the face of the user.

Heated humidification has been shown to enhance patient comfort. In some embodiments of the invention, the system incorporates heating to create heated humidification for the user. Conventional humidifiers heat large masses of water and allow air to pass over them to create heated humidification. The invention described here allows for the active heating of the moisturized air. In some embodiments, the mist itself is heated by a heating element incorporated in the ultrasonic unit. The fluid may be heated in its reservoir, while it travels from the reservoir to the humidification element, in the small antechamber to the humidification element, by the humidification element itself, or once it is inside the air path tubing, or some combination thereof. Heating smaller amounts of water just before, during or after transformation into mist is more efficient than maintaining an entire reservoir at temperature. Heating elements incorporated in the tubing heat the mist and air as it passes by. A combination of heating the water prior to vaporization and heating the mist in the air path may offer the most efficient results.

Heating is achieved through the use of a heating element. The heating element can be a resistance heater, such as a wire. The material can be metal or a composite material. The heating element can take on several different geometries. Coiled wire offers increased surface area for improved heat transfer. Other heating geometries which maximize heat transfer can be employed. One particular geometry of interest allows laminar flow and a high surface area for heat transfer. This is achieved by forming multiple longitudinal channels that create multiple parallel air paths, leading to laminar flow and allowing for significantly increased surface area for heating. Exposure of the air path to the heating element can be optimized from a cross-sectional perspective, as well as a longitudinal perspective. This allows for the maximum heat transfer in the smallest possible device size.

A combination of heating both the water on its way to the humidification element and the air in the air path can offer the best heat profile, comfort, and efficiency.

Several materials can be used to insulate the heating elements of the system from the other components. These materials include but are not limited to: ceramics, silicones, heat tolerant polymers, polyimides, and other material with adequate heat resistant properties.

According to another aspect of the present invention, fluid must be transported from a separate reservoir to an integrated humidification tube.

For this purpose, a small pump can be provided with the system to pump water from the reservoir to the humidification element. This micro pump can operate continuously, or be tuned to deliver water only as needed. Further, the pump can be adapted to deliver water timed with the respiratory cycle. Thus, when a user inhales, the inhaled air can be well humidified, while during the rest of the respiratory cycle the air need not be humidified. The humidification system may contain sensors to sense the respiratory cycle to enable the timing of the humidification. These sensors may include pressure, flow, or temperature sensors. The humidification device may alternatively communicate with the flow generator machine to utilize its sensors to indicate the timing of the respiratory cycle. This timing helps save water, energy, and reduces the negative side effects of rainout from too much water condensing and collecting in the airflow tubing. Excess water can impede airflow, and if it drips onto the user's face, it causes an unpleasant arousal from sleep and deters usage of the PAP device.

According to one embodiment of the invention, gravity is used to move the water from the reservoir to the humidification element. By placing the water reservoir at a higher level than the humidification element, water will flow to the humidification element, keeping it supplied with water. This rate can be regulated by the height difference between the reservoir and the humidification element, or by the incorporation of flow restricting elements in line. The ultrasonic element can be designed with micro holes, such that the water does not flow through it unless it is activated. This prevents forward flow from the reservoir through the humidification element and into the air path when not desired, thereby inherently regulating the rate of fluid flow.

According to another embodiment of the invention, weight or pressure can be used to transport the water from the reservoir to the humidification element. The water reservoir is in the form of a flexible bladder. This bladder is placed under a weight, thereby pressurizing it enough to drive fluid flow to the humidification element. One such way to achieve this weight is by placing the reservoir bladder under the sleeper. It could be placed under the pillow or the mattress. Alternatively, the fluid bladder is pressurized by placing it within an inflatable sleeve. Inflation of the sleeve exerts pressure on the fluid bladder, driving fluid flow to the in-line humidifier. Alternatively, the fluid bladder itself can be pressurized by pumping air into it with a pump. Pumps can be automated, hand-driven, or simple one-way valve structures used to inflate the fluid bladder.

According to another embodiment of the invention, wicking materials provide a method to transport fluid from the reservoir to the humidification element. Wicking materials pull fluid from the reservoir to the humidification element. As the fluid is converted to humidity, more fluid is drawn from the reservoir to replace it. This approach has the advantage of being low power. The materials provide for the movement of the water, without needing additional energy. Furthermore, it does not require that the reservoir be necessarily placed higher than the humidification element.

Combinations of the above approaches to move water from the reservoir to the humidification element are also possible, and may offer distinct advantages. For example, a pumping system which includes wicking matrix material in the line can help regulate the rate at which the fluid is transported through the system. This can help avoid under or over transporting water to the humidification element. Likewise, gravity and wicking aspects could be combined to offer a system that requires no additional power to move water and is also self-regulating.

For reasons described above, means for filtration and purification of the water is desired. For ultrasonically based systems, distilled water can be used. If regular tap water is used, a filtration material can be incorporated to remove minerals inherent in the water.

According to another embodiment of the present invention, a filtration media is incorporated into the system between the fluid reservoir and the humidification element to remove undesired substances from the water. In one embodiment, the filtration involves a demineralization filter. This filter removes minerals in the water, producing water that is free of particulate contaminants and suitable for consistent respiration. This allows for the use of tap water in the system. Tap water often contains minerals that are not desirable to be aerosolized and inhaled. There are filtration media with demonstrated performance in removing minerals from water. Suitable media include those commonly found in water filtration applications such as reverse osmosis systems, steam cleaning apparatus, aquarium filtration and water softeners. The ability to use tap water is a significant advantage, particularly in the travel environment, as it can be difficult and burdensome to locate a source of distilled water when travelling. It is certainly inconvenient, and in some cases not possible, to travel with large amounts of distilled water. The ability to use tap water in the humidification system is a significant advancement.

This filter can be placed inside the adaptor which threads onto the fluid reservoir. This filter location prevents minerals from entering the rest of the system, keeping it cleaner and safer. Additionally, the filter can be easily changed from such a position, and also has the opportunity to dry out between uses if desired. The filter can alternatively be placed at the terminus of the hose inserted into the fluid reservoir. The filter may also be placed anywhere along the fluid path between the fluid reservoir and the humidification hose.

A demineralization filter can be achieved compactly, as the volume of water to be demineralized is relatively small compared to other common applications. Demineralization resins offer efficacy adequate to treat a year's worth of humidification water with a few ounces of material or less. In a further embodiment, the demineralization material can change colors to indicate to the user when it is time to replace the filter.

Demineralization can be achieved using reverse osmosis. High pressure is applied through semi-permeable membranes which remove minerals. Demineralization can also be achieved through the use of resins which exchange the minerals that make the water hard, such as calcium and magnesium ions, with other, softer ions such as sodium or potassium. Resins may be in the form of gel beads comprising cross-linked polystyrene, divinylbenzene, or similar materials. In another embodiment, electrodeionization can be used to remove minerals from the water—a process utilizing resins, semi-permeable membranes, and electricity to remove unwanted ions and minerals.

According to another embodiment of the invention, sterilization and purification elements are incorporated into the system. An ultraviolet light source is utilized to disinfect the water. Ultraviolet light has been demonstrated to kill microorganisms that may develop in a fluid environment. UV light will kill fungi, mold, bacteria, viruses and other potentially problematic growth organisms. This feature ensures greater safety for the user, and also provides ease of use. Typical humidification systems recommend that the user perform regular and time-consuming cleanings of the device. Due to the burden of such cleanings, many users do not regularly or adequately clean their systems. A self-cleaning and self-regulating system offers significant advantages to the user in both safety and convenience. The UV light source can be incorporated in the fluid reservoir, along the fluid path from the reservoir to the humidification element, within the humidification element, or inside the hose with the humidified air path. In one embodiment, the UV light source is provided in the antechamber of the humidification element. The UV light prevents growth of microorganisms and helps keep the unit clean, further reducing the maintenance burden on the user.

According to another embodiment of the invention, antibacterial and anti-microbial materials or coatings are incorporated into the system to slow or prevent the growth of microorganisms. These materials and coatings are placed along the fluid and air path.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
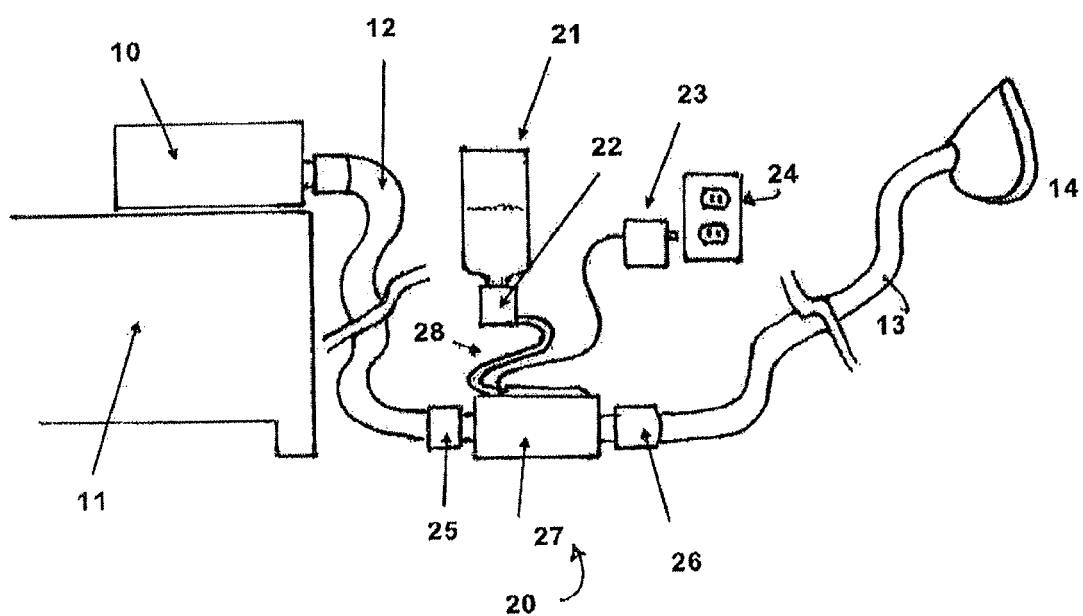
FIG. 1 illustrates one embodiment of a portable humidification system for a PAP system according to this invention.

FIG. 1 illustrates one embodiment of a portable humidification system for a PAP system according to this invention. A flow generator 10 produces pressurized airflow, which passes through a lumen of a first air conduit section 12 connecting the flow generator to a humidifier 27, where it is humidified and then continues traveling through a lumen of an air conduit section 13 to a patient interface 14, such as a mask or a nasal cannula. Humidifier 27 is integrated with, and supported by, the air conduit 12/13. As shown, the flow generator 10 is resting on a table 11 or other surface.

Humidifier 27 is part of a portable humidification system 20. In addition to the humidifier 27, the portable humidification system 20 has a fluid reservoir 21, a humidifier inlet 25, a humidifier outlet 26, a power source connection 23, and a conduit 28 connecting the fluid reservoir 21 to humidifier 27 through an optional reservoir adaptor 22. The fluid reservoir 21 is filled with the desired humidification fluid, in many cases distilled water, undistilled water, tap water, and bottled water. The fluid reservoir 21 is pictured situated above the tubing integrated humidifier 27, such that the fluid will flow from the reservoir to the humidifier by means of gravity. In this embodiment, the portable humidification element 20 may be powered via the power connection 23, shown here as accessing a wall power outlet 24. Alternatively, other power sources, such as batteries, may be used.

Figure 2:
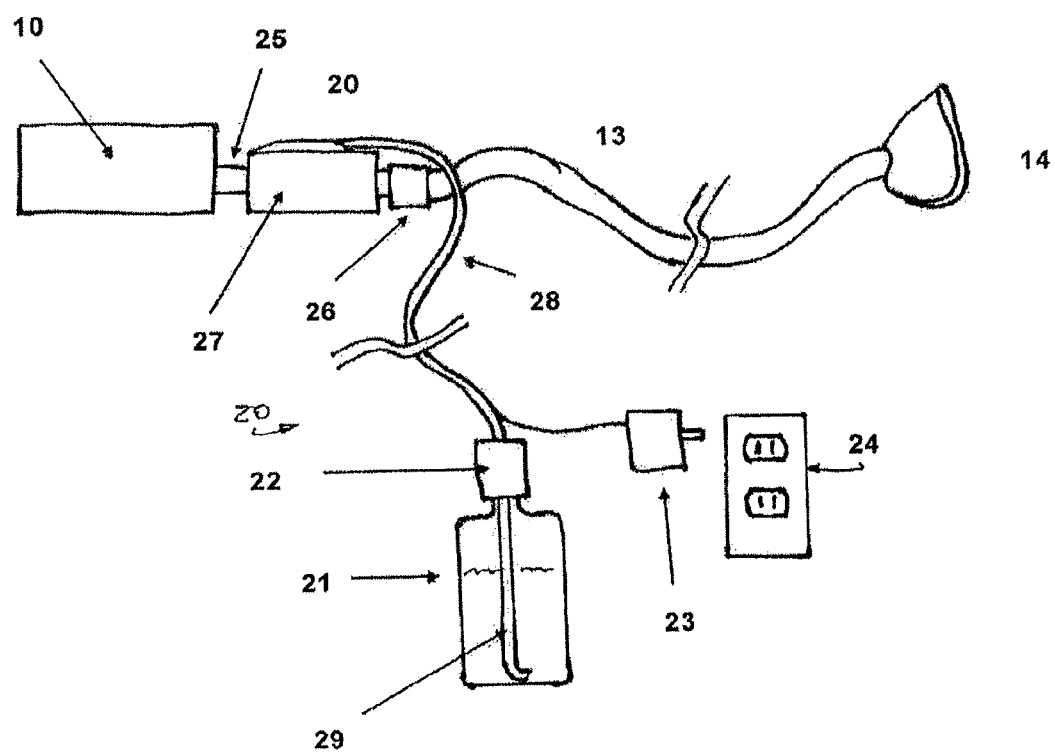
FIG. 2 illustrates another embodiment of a portable humidification system according to the invention.

FIG. 2 illustrates another embodiment of a portable humidification system according to the invention. Here the fluid reservoir 21 is shown lower than the tubing integrated humidifier 27. In this embodiment, a pump (not shown) integrated into the system at either the reservoir adaptor 22 or the tubing integrated humidifier 27 provides the means to transport the fluid from the fluid reservoir 21 to the tubing integrated humidifier 27. This allows the system to operate independent of gravity.

Figure 3:
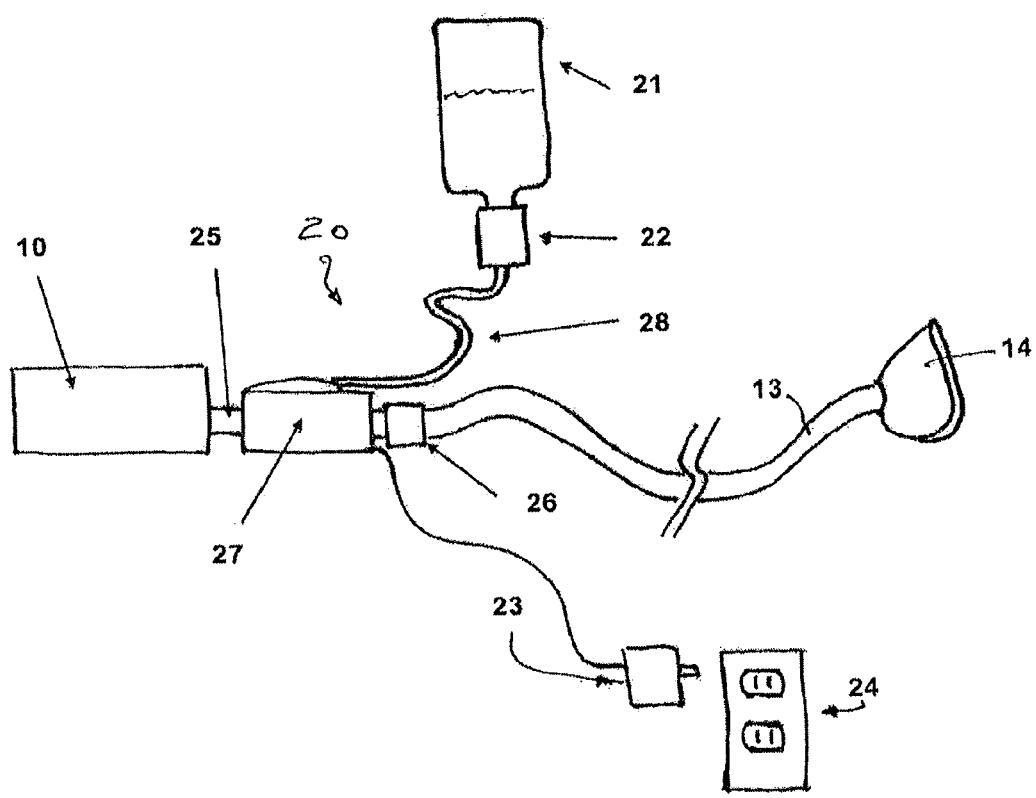
FIG. 3 illustrates yet another embodiment of a portable humidification system according to the invention.

FIG. 3 illustrates another embodiment of a portable humidification system according to the invention. In this embodiment the tubing integrated humidifier 27 is placed in close proximity to the flow generator 10. This arrangement allows the tubing 13 connecting the humidifier to the patient interface 14 to be standardized. Power for the humidifier 27 can be supplied via the power cord 23 to a power outlet 24 as shown. Alternatively, power for the humidifier 27 can be routed through the flow generator 10.

Figure 4:
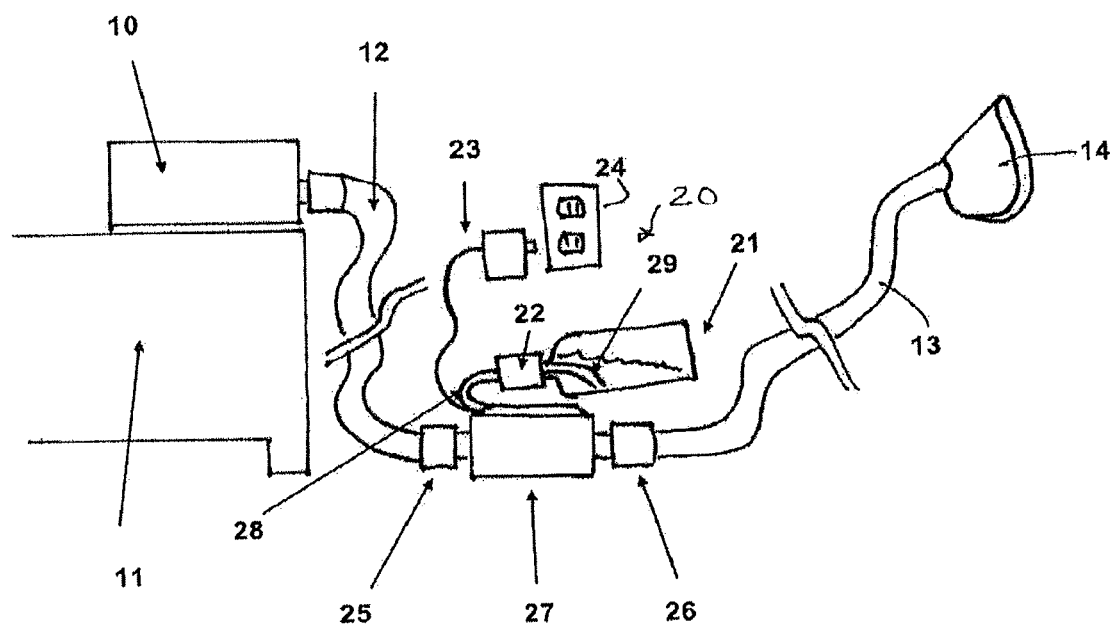
FIG. 4 illustrates still another embodiment of the portable humidification system according to this invention.

FIG. 4 illustrates another embodiment of the portable humidification system according to this invention. In this embodiment the fluid reservoir 21 is situated on its side. This arrangement can allow for the portable humidifier 27 and the fluid reservoir 21 to be placed out of the way of the user, for example on the floor. Fluid reservoir intake tube 29 is positioned in the fluid reservoir 21 to pull fluid for transport to the humidification element.

Figure 5:
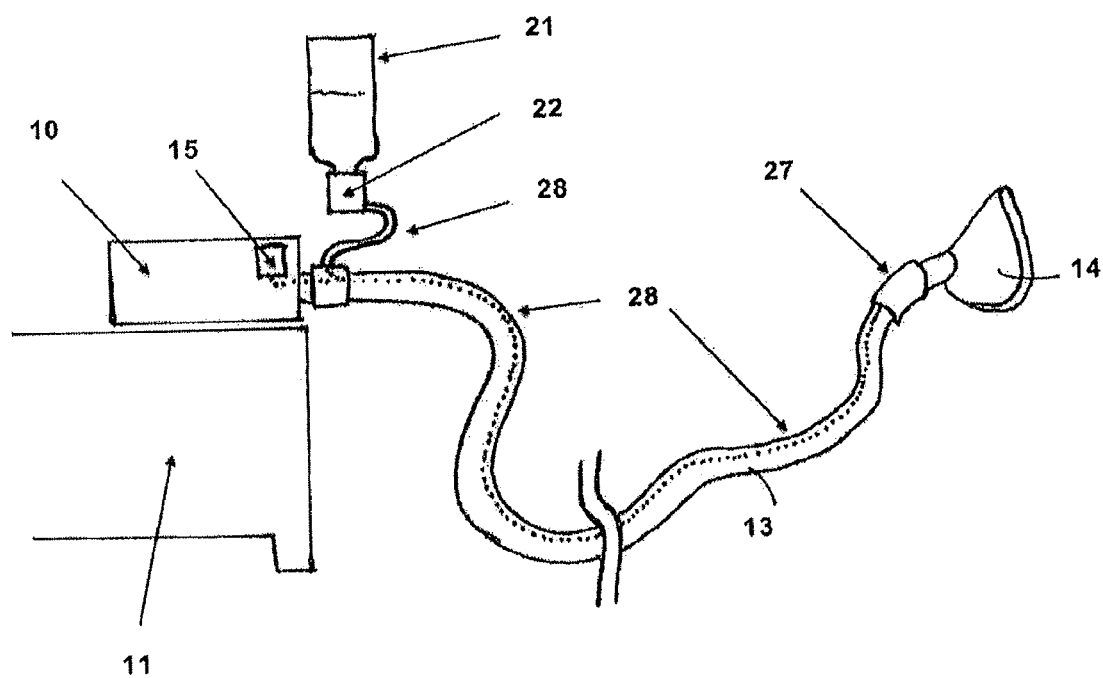
FIG. 5 illustrates yet another embodiment of the portable humidification system according to this invention.

FIG. 5 illustrates another embodiment of the portable humidification system. In this embodiment the fluid reservoir 21 is placed higher than the tubing integrated humidifier 27. This allows gravity to provide the force for fluid to flow from the fluid reservoir 21, through the reservoir adaptor 22, through the reservoir tubing 28, of which a portion of the reservoir tubing 28 is here shown to be collocated alongside the air conduit 13. The fluid is delivered to the tubing integrated humidifier 27, and humidification is provided very close to the user interface 14. This setup provides the advantage of providing the humidification in close proximity to the user. In some embodiments, the humidification can occur just proximal to the patient interface, as little as about 1 cm or less from the mask. In some embodiments, the humidification can occur between about 5 and 50 cm from the user interface. This reduces the incidence of excess humidification, reduces rainout, and reduces the amount of tube heating required to prevent rainout. Additionally, the tubing integrated humidifier 27 can communicate, either wired or wirelessly, with the flow generator 10 to selectively cycle on and off, providing humidification only during the part of the respiratory cycle (inspiration, expiration) when it is needed. This increases the efficiency of the system, both from an energy standpoint and from a water use standpoint. This selective cycling further reduces the incidence of rainout.

Figure 6:
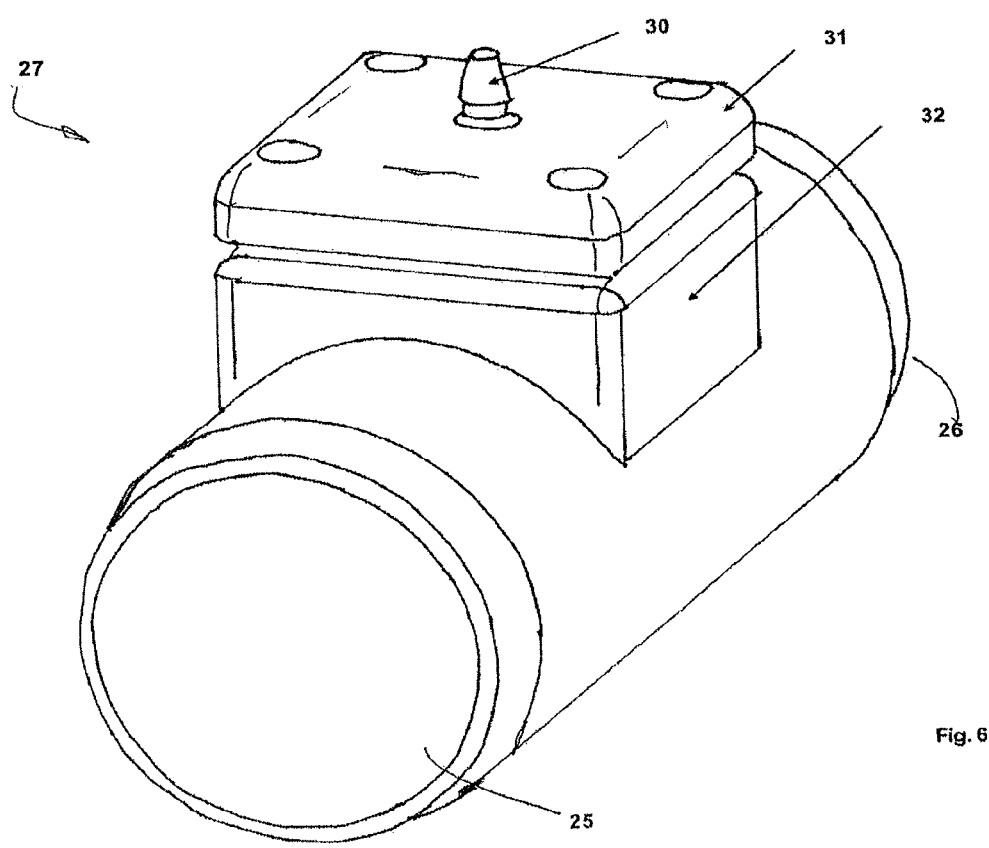
FIG. 6 illustrates an embodiment of a portable humidifier according to this invention.

FIG. 6 illustrates an embodiment of a portable humidifier 27 according to this invention. This tubing integrated humidifier 27 has an inlet 25 and an outlet 26 for the flow of air through the tubing section. Also shown is an inlet port 30 for the humidification chamber, where the fluid is introduced. The humidifier lid 31 seals against the humidifier chamber housing 32.

Figure 7:
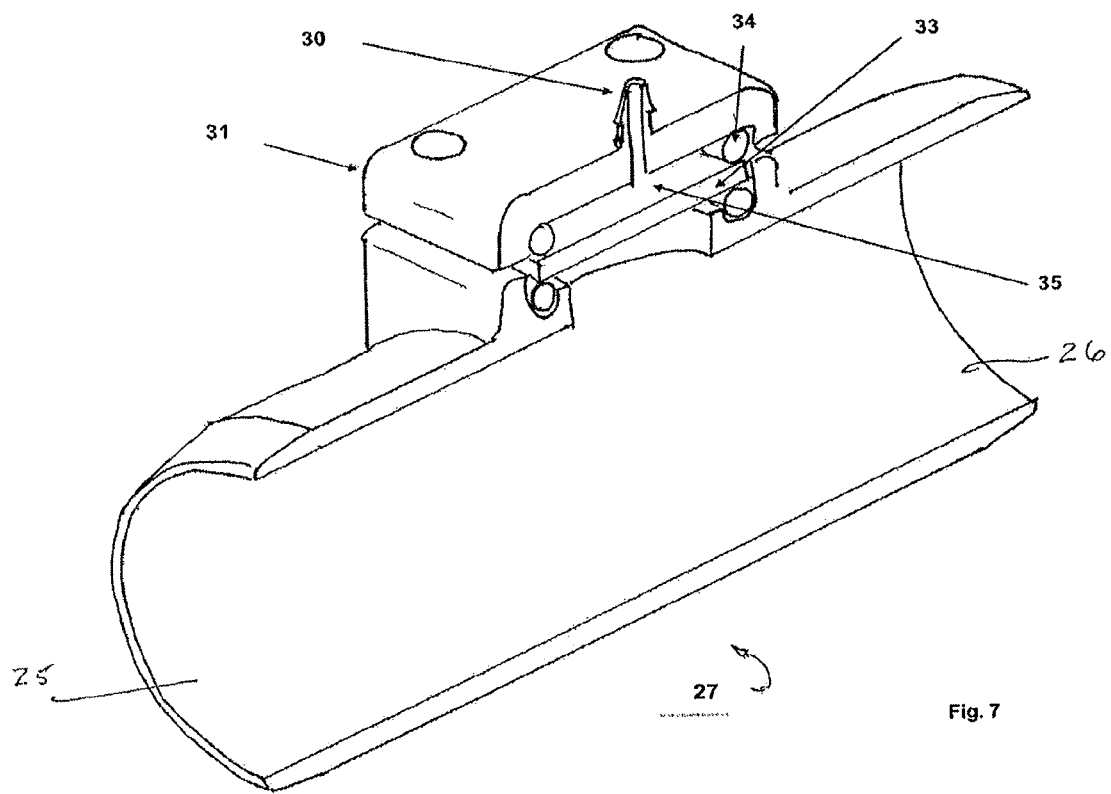
FIG. 7 is a longitudinal cross-sectional view of the portable humidifier shown in FIG. 6.

FIG. 7 is a longitudinal cross-sectional view of the portable humidifier 27 shown in FIG. 6. This further illustrates the fluid inlet port 30, which delivers fluid to the humidification chamber 35. Note the relative small size of the humidification chamber 35. This is a significant advantage and greatly enhances the portability of the system. Also shown here is the humidification element 33. In one embodiment, this element is an ultrasonic element, such as a nebulizer, which vibrates to create the humidity. Also pictured are several sealing elements 34.

Figure 8:
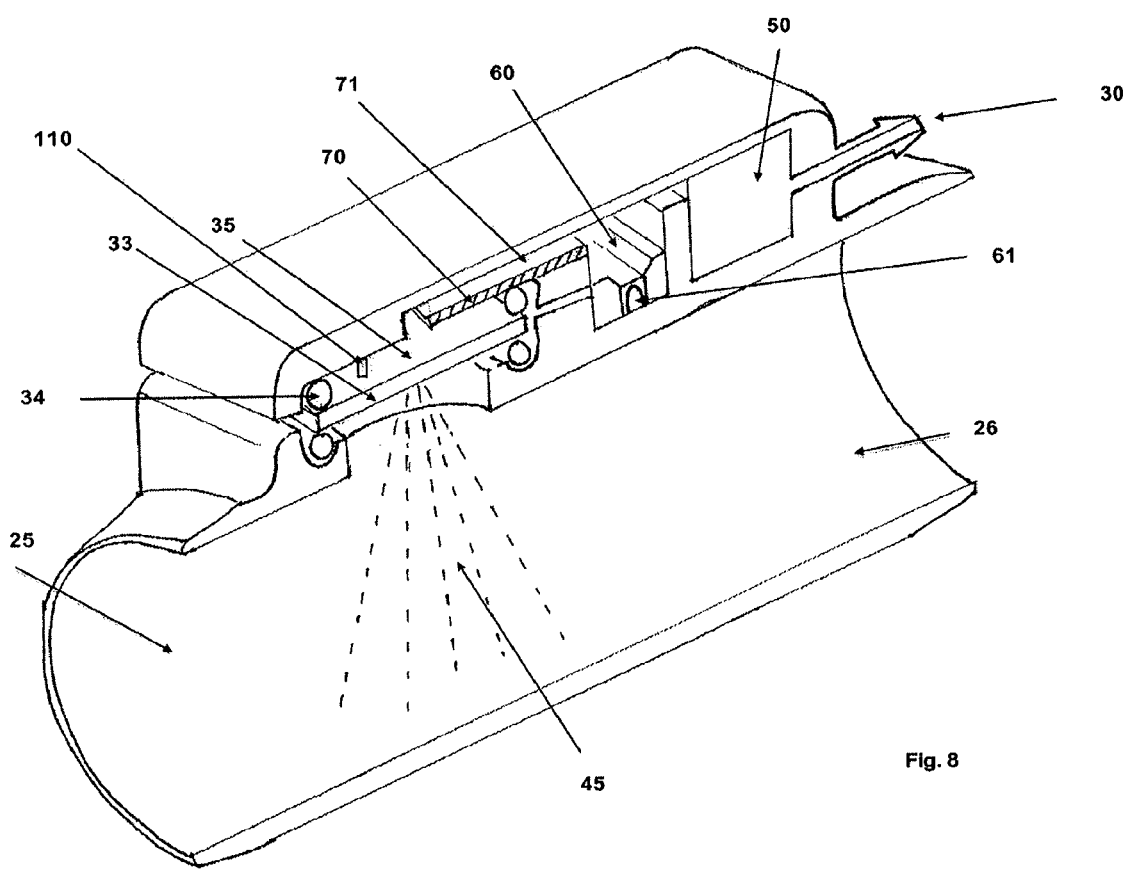
FIG. 8 is a longitudinal cross-sectional view of yet another portable humidifier according to this invention.

FIG. 8 is a longitudinal cross-sectional view of yet another portable humidifier 27. Here the fluid is introduced through the inlet port 30. It enters the integrated pump 50, which drives the fluid flow, pulling it from a fluid reservoir (not shown) and pushing into an optional ultraviolet (UV) sanitization chamber 60 where there is a UV light source 61 to kill microorganisms in the fluid as they pass through the UV treatment chamber 60. This UV light source 61 could be a UV LED. From there, the fluid passes through a fluid channel 71, which takes the fluid along an optional heating element 70 which heats the fluid as it enters the humidification chamber 35. An optional fluid sensor 110 is shown monitoring the fluid level in the humidification chamber 35. This fluid sensor 110 senses the presence of fluid in the chamber, and can relay these findings to regulate the control of the pump to maintain the desired fluid level in the chamber. The resultant heated, sanitized humidification is shown here as 45.

Figure 9:
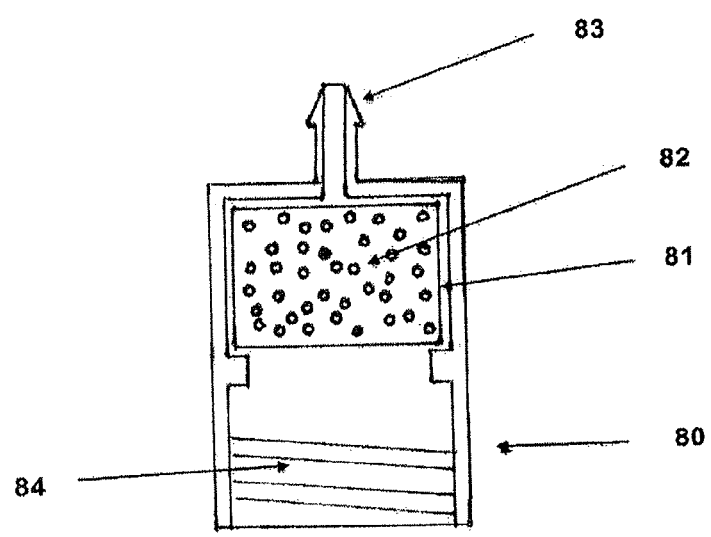
FIG. 9 is a cross-sectional view of a fluid reservoir adaptor according to this invention.

FIG. 9 is a cross-sectional view of a fluid reservoir adaptor. The adaptor 80 includes threads 84 allowing it to attach to standard water bottles and other reservoirs. Incorporated in the adaptor is a filtration chamber 81, which houses filtration media 82. Filtration media can filter the fluid for impurities. One embodiment has the filtration media including demineralization media. This allows the user to utilize tap water in the system. The demineralization media removes any minerals in the tap water prior to aerosolization for humidification. This provides significant safety and convenience for the user.

Figure 10:
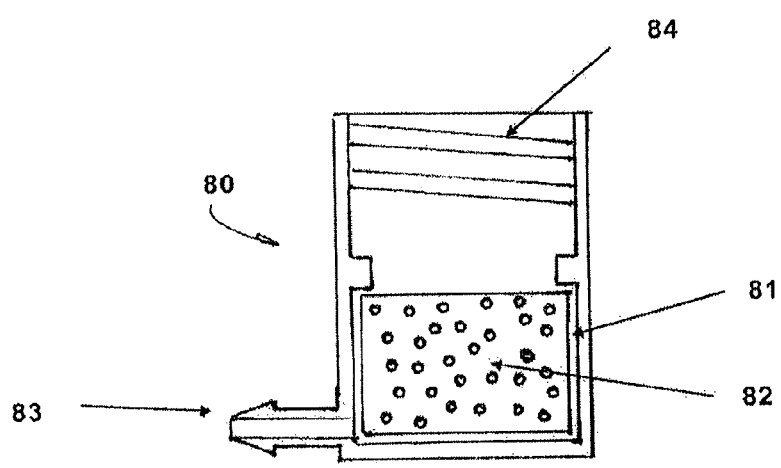
FIG. 10 is a cross-sectional view of the fluid reservoir adaptor of FIG. 9, showing an alternative outlet geometry for the fluid reservoir outlet.

FIG. 10 is a cross-sectional view of the fluid reservoir adaptor 80, showing an alternative outlet geometry for the fluid reservoir outlet 83.

Figure 11:
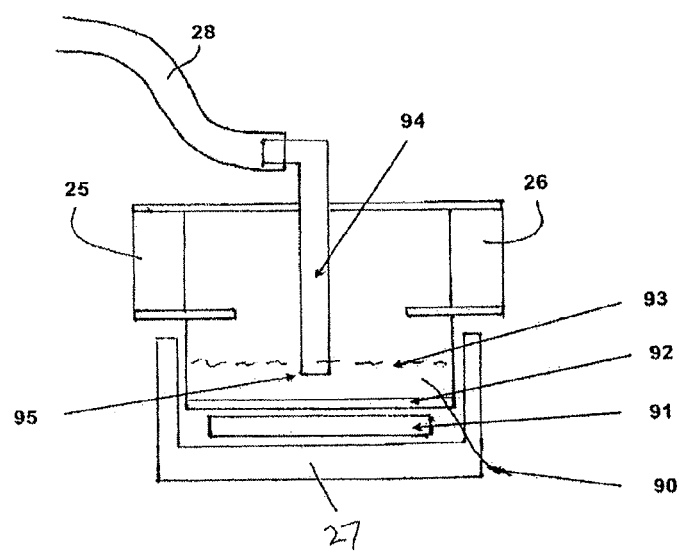
FIG. 11 is a cross-sectional view of a portable humidifier component according to another embodiment of the invention.

FIG. 11 is a cross-sectional view of a portable humidifier component according to another embodiment of the invention. As in other embodiments, the tubing integrated humidifier 27 connects to an air conduit (not shown) via inlet 25 and outlet 26. This design utilizes a heating element 91, which is housed in a base structure. Heat from the heating element 91 is transfer through a heat transfer material 92, which is integrated into a small fluid chamber 90. The level of fluid 93 in chamber 90 is low, allowing for the heating element to only heat a small amount of fluid at a time. This is more efficient and does not require the heating and maintaining the heat of a large reservoir of fluid as most conventional humidifiers do. A fluid replenishment tube 94 connected to the fluid reservoir (not shown) via fluid conduit 28 has an outlet 95 which is a fixed distance from the bottom of chamber 90. When the heated fluid evaporates into the airflow, the level of fluid 93 will drop below the outlet 95 of the fluid replenishment tube 94. When this occurs, air is allowed to pass up the fluid replenishment tube to the large fluid reservoir (not shown), thereby allowing more fluid to enter the chamber, up until the point where the outlet of the fluid replenishment tube is again submerged. This effectively creates a self-regulating, self-replenishing system. The small amount of fluid to be heated enables a much more efficient system.

Figure 12:
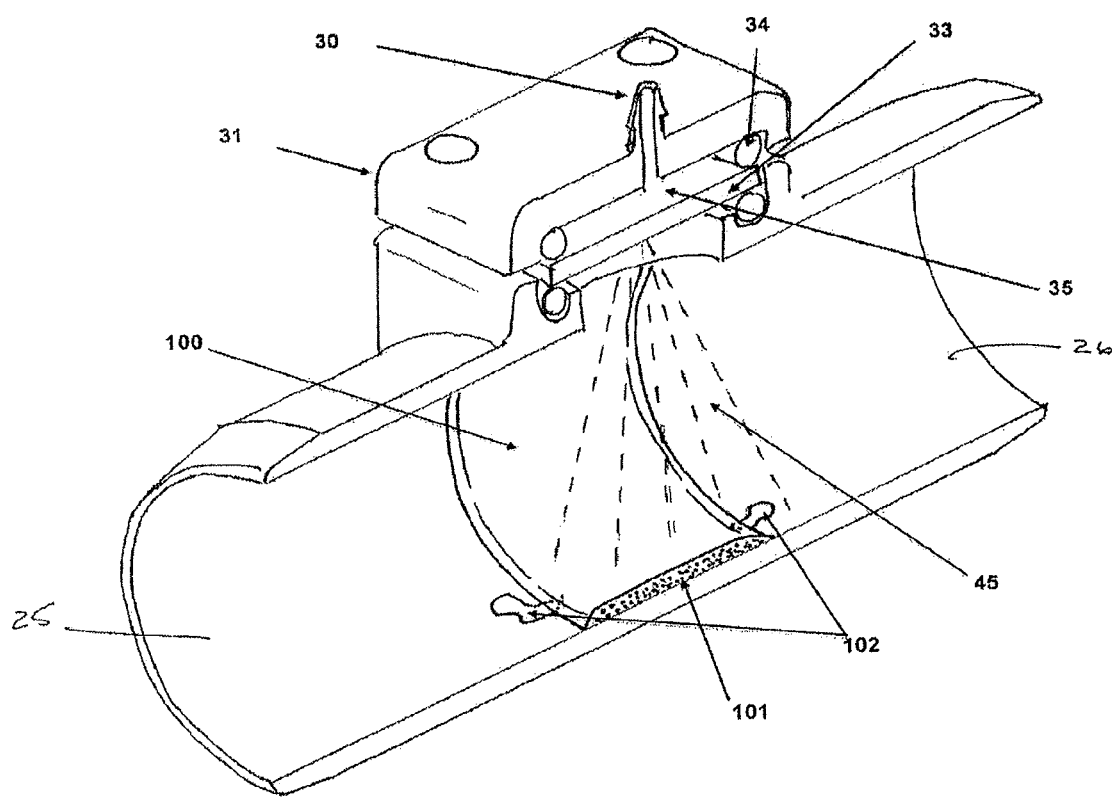
FIG. 12 is a longitudinal cross-sectional view of a portable humidifier according to another embodiment of the invention.

FIG. 12 is a longitudinal cross-sectional view of a portable humidifier according to another embodiment of the invention. The fluid inlet port 30 delivers fluid to the humidification chamber 35. Note the relative small size of the humidification chamber 35 with respect to the diameter of the air conduit formed in part by connectors 25 and 26. The humidification chamber 35 can hold a volume of about 0.1 cc to 5 cc of water. In one embodiment, the humidification chamber holds about 0.5 cc of fluid. This small size is a significant advantage as it greatly enhances the portability of the system compared to conventional systems for humidification, which typically are sized to hold 350 cc to 500 cc. Also shown here is the humidification element 33. In one embodiment, this element is an ultrasonic element, such as a nebulizer, which vibrates to create the humidity 45. Also pictured are several sealing elements 34. An absorbent element 100 is shown lining a portion of the interior of the airflow lumen. The absorbent element 100 is comprised of an absorbent material 101, such as hydrogels, fibers, cottons, synthetics, polymers, superabsorbent polymers, polyvinyl alcohols, and other materials known to be absorbent. This absorbent material 101 may also be wicking. This material removes excess moisture, especially condensate 102, from the airflow lumen. In one embodiment, the absorbent material 101 absorbs excess moisture and then wicks it back to the humidification element 33 to be aerosolized once again.

Figure 13:
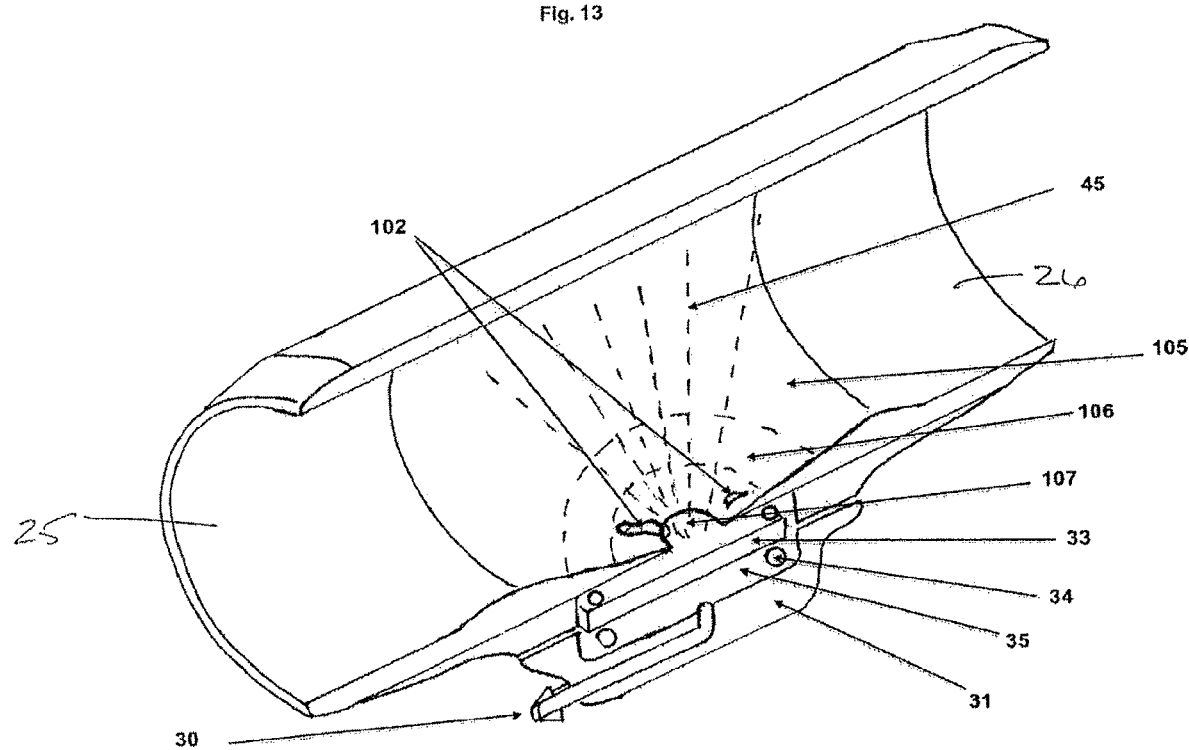
FIG. 13 is a longitudinal cross-sectional view of a portable humidifier according to yet another embodiment of the invention.
Figure 14A:
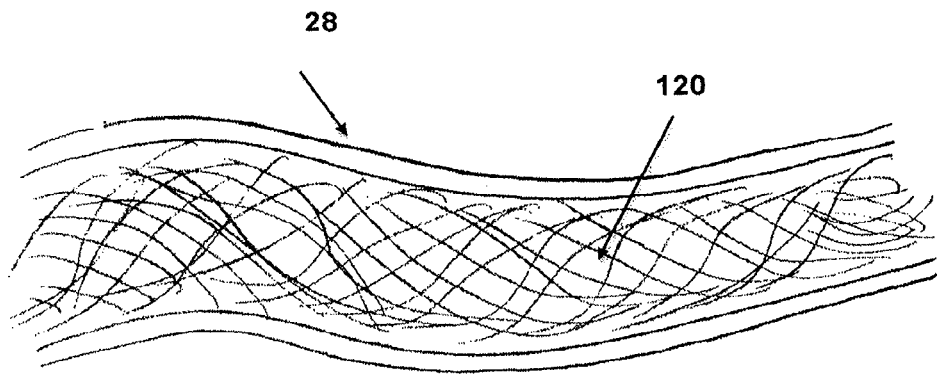
FIGS. 14a, b, and c are diagrammatic cross-sections showing various embodiments allowing wicking and regulation of fluid flow from the fluid reservoir to the humidification element.
Figure 14B:
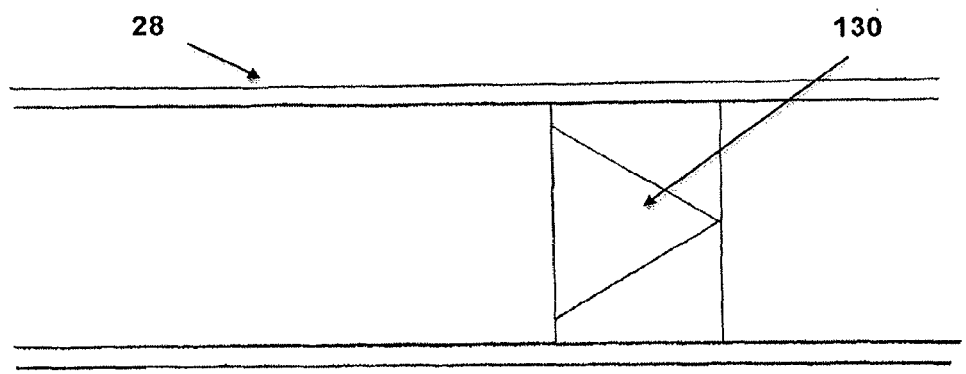
Figure 14C:
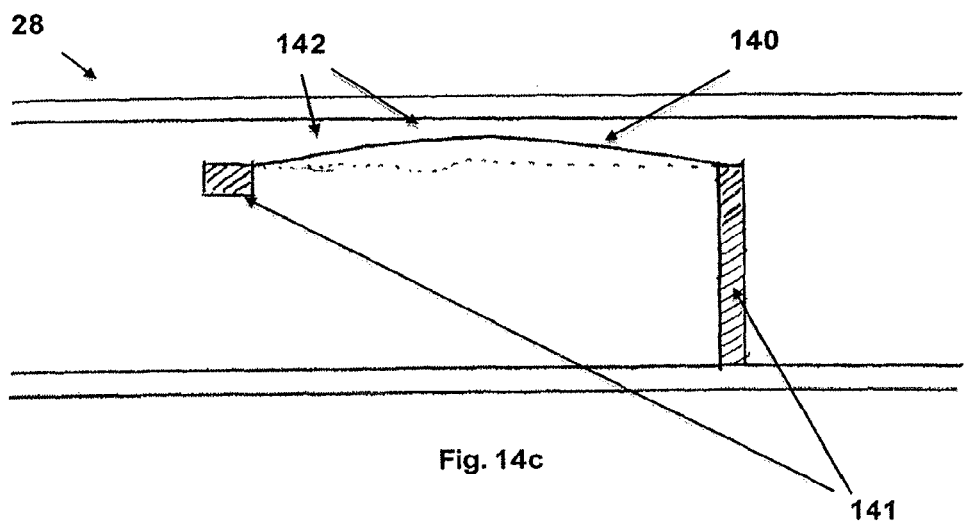
Figure 15:
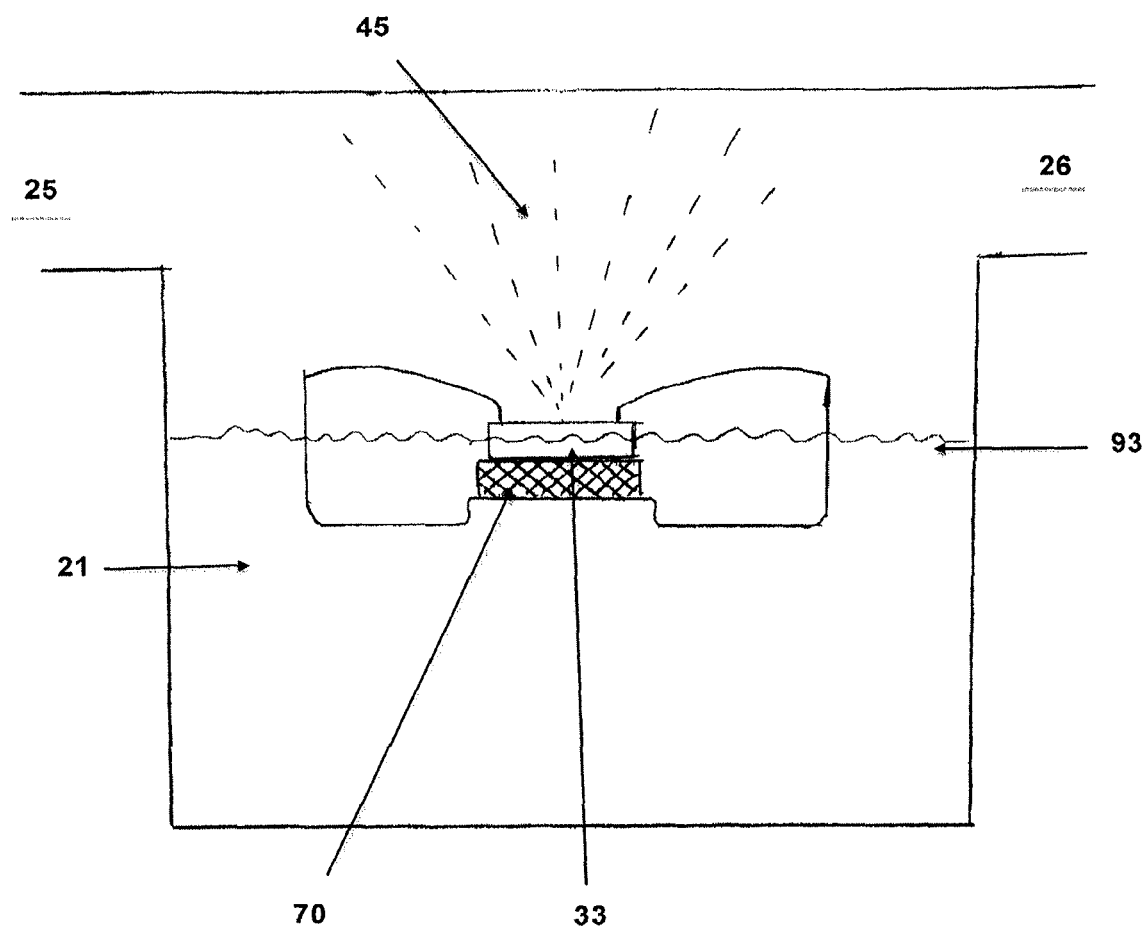
FIG. 15 shows a cross-sectional side view of an alternative embodiment for the humidifier of this invention

FIG. 13 is a longitudinal cross-sectional view of a portable humidifier according to another embodiment of the invention. The fluid inlet port 30 delivers fluid to the humidification chamber 35. The humidification element 33 (such as, e.g., an ultrasonic nebulizer) transforms the fluid into humidity 45. A condensate collection element 105 is shown lining a portion of the interior of the air flow lumen. This condensate collection element 105 is designed to collect excess moisture in the form of condensate 102, and the concave condensation channel 106 channels the condensate 102 back through the aperture for the return of condensate 107 to the humidification element 33 to be aerosolized once again. This allows excess moisture, especially condensate 102, to be removed from the airflow lumen and aerosolized again. In this way, the systems depicted in FIGS. 12 and 13 are self-regulating, allowing for the optimum humidity to be maintained in the system. One embodiment of the system as depicted in FIG. 13 requires orientation relative to gravity such that the fluid drains naturally via the concave condensation channel 106 to return to the humidification element 33, when it is positioned on the bottom side of the tubing as shown in FIG. 13.

FIGS. 14*a, b*, and *c* are diagrammatic cross-sections showing various embodiments allowing wicking and regulation of fluid flow from the fluid reservoir to the humidification element. FIG. 14*a* shows a cross-sectional side view of the tubing 28 connecting the fluid reservoir to the humidifier with a wicking material 120 in the lumen to wick fluid from the reservoir to the humidification element. FIG. 14*b* is a diagrammatic cross-sectional side view of the tubing 28 connecting the fluid reservoir to the humidifier with a fluid valve 130, which could be one of many such valves, to aid in the transport of fluid from the reservoir to the humidifier. A combination of wicking material and valves can provide for the transport of fluid. The one-way valves with a low cracking pressure allow for ease of forward flow while preventing back flow of fluid. FIG. 14*c* is a diagrammatic cross-sectional side view of the tubing 28 connecting the fluid reservoir to the humidifier, with a self-regulating flow limiting structure included. The structure includes a deflectable member 140, attached to rigid members 141. The fluid flow channel 142 is sized to allow a flow rate up to the maximum desired flow rate. When the pressure in the fluid tube 28 increases, the pressure deflects the deflectable member 140, further restricting the fluid flow channel 142, thereby keeping the flow rate within the desired range. When the pressure in the fluid tube 28 is reduced, the deflectable member flexes back down, thereby increasing the lumen of the fluid channel 142, allowing greater flow. In this manner, the structure shown in FIG. 14*c* allows for the self-regulation of the flow rate from the reservoir to the humidifier. This embodiment can be particularly useful when the reservoir is placed higher than the humidifier and gravity provides the primary driving force for delivering fluid from the reservoir to the humidifier. This structure helps regulate fluid flow and prevent flow rates above a desired maximum flow rate.

FIG. 15 shows a cross-sectional side view of an alternative embodiment for the humidifier. The humidification element 33 is mounted within a floating structure which has a portion of its structure above the fluid level 93, and a portion below. The humidification element 33 sits right at the fluid level 93, such that it can access fluid from below consistently and create humidity 45 into the air above for transport within the air circuit. The humidifier inlet 25 and humidifier outlet 26 communicate with the rest of the tubing to provide the humidified airflow to the user. An optional integrated heating element 70 is also pictured, just below the humidification element. The heating element 70 heats the fluid to the desired temperature prior to the humidification process. This entire humidification structure sits within the fluid reservoir 21. As the fluid level 93 drops, the humidification structure drops with it, remaining on the surface. This embodiment offers several advantages. There is no need to transport fluid from a reservoir to the humidification element. There is no need to heat the entire fluid reservoir. The humidification element always has access to fluid for humidification. This embodiment offers an alternative integrated humidifier design.

A preferred embodiment of the system achieves humidification through the use of an ultrasonic humidification element. This can entail a piezoelectric material that oscillates at ultrasonic frequencies to create tiny droplets of water, or mist. This approach offers several advantages. Ultrasonic elements can be made with a very small size, making them particularly well suited for portable applications. Additionally, they are relatively efficient in power use compared to other humidification technologies. Ultrasonic humidification can be realized in multiple ways. In one approach, the oscillating element is placed beneath a small amount of water, and when it vibrates the droplets are emitted from the surface of the water. In another form, the vibrating element has micro holes that allow for the passage of water from a reservoir side to the opposite side where it is converted into droplets of airborne water. Vibrating elements with holes can be more efficient as they do not require the energy to pass through a mass of water to achieve the humidification. An additional advantage of ultrasonic humidification elements is their low cost.

An alternative embodiment utilizes a jet nebulizer to achieve humidity in the airflow. A compressed air source is used to force air through water at a high velocity, resulting in tiny droplets of water being aerosolized. This system can use pressurized air selectively, timing its release as needed to humidify the airstream.

An alternative embodiment utilizes a fluid introduction element with micro perforations to introduce water to the airflow. By introducing tiny droplets of water in a multitude of locations, the passing air becomes humidified.

An alternative embodiment utilizes a wicking element that humidifies the airflow through evaporation. Various materials can be used, from papers, to fibers, fabrics, ceramics and matrices of polymers can be used to wick moisture from a source and into the air stream. By increasing the amount of surface area for evaporation, the amount of humidification can be influenced. Wicking elements have an advantage of being self-regulating. When the relative humidity is high, evaporation occurs at a slower rate, thereby regulating the overall humidity to the user.

An alternative embodiment combines a weeping element with a porous dispersion material. The porous dispersion material is similar to a sponge. The dispersion material is saturated with water, and includes geometry to maximize its surface area and the creation of tiny droplets of water. These droplets disperse into the airflow.

An alternative embodiment utilizes on demand heating for more efficient heated humidification. Prior art humidification systems utilize a hot plate heating element that heats up a large enough volume of water to last through the night. This approach has several limitations. It takes some time for the heating element to bring the entire volume of water up to the desired temperature. It requires additional energy to keep the entire volume of water at temperature. These shortcomings can be overcome with on demand heating technology.

A small heating chamber is used to heat enough water to meet the evaporation and humidification demand of the system. This chamber is continually replenished from a larger reservoir of water. This larger reservoir does not need to be heated, saving energy. Only the relevant amount of water is heated, as it is needed. As the water in the small heating chamber evaporates, it is replenished from the reservoir. Multiple replenishment mechanisms can be used. Gravity can be used to replenish the heating chamber. This can be accomplished in a self-regulating way by having a refill tube enter the heating chamber vertically from above, and stop short of contacting the base of the chamber interior. With the water reservoir sealed, the water will only come out of the refill tube when it can be replaced by air from the heating chamber. This occurs once the water level in the heating chamber dips below the level of the tube opening. When the water level falls below the level of this opening, air will be allowed into the reservoir, and water will leave the reservoir until the tube opening is once again submerged in water. This auto refill system ensures a steady, self-regulating amount of water in the heating chamber.

In another embodiment, the water level in the heating chamber is refilled through the use of a pump 50. This approach can incorporate an optional sensor system. A fluid sensor 110 placed at the desired level in the heating chamber provides information on the fluid level, which is used to determine whether the chamber needs more water. A pump or valve system is then controlled to allow the desired amount of water to pass from the reservoir to the heating chamber. A depiction of this is included in FIG. 8.

As described above, a way to transport water from the reservoir to the heating chamber is through the use of a wicking material. A wicking material placed in the conduit between the reservoir and the heating chamber transports water from the reservoir to the chamber. The wicking rate can be controlled by varying the wicking material, it's density, and the geometry of the conduit. Rate limiting valves can also be employed to affect an upper limit on the rate of water transfer. Pumps, gravity, or pressurizing the reservoir can also be used in conjunction with wicking to achieve the desired fluid transfer rate.

Another embodiment of the invention utilizes a floating humidification element in the water reservoir. This eliminates the need to transport water from the reservoir to the humidification element. It also eliminates the need to heat the entire reservoir of water. An element which performs humidification and optionally also heating is placed in a structure which floats on the surface of the water. The floatation element is designed such that a portion of the structure is kept above the water level, and another portion is below the water level. Water is sourced by a pathway in the portion of the structure which is submerged. This allows the device to maintain the optimum desired level of water in the humidification element. As the water reservoir empties throughout use, the floating structure simply lowers, staying on the surface of the water. FIG. 15 is a depiction of this embodiment.

Any combination of the above described humidification elements is possible, and in many cases will be most desirable. For example, an ultrasonic element with a wicking material will distribute moisture evenly and consistently. Also, while the invention has been described with reference to PAP devices, the invention is also applicable to CPAP, XPAP, BiPAP, APAP and AutoPAP devices.

Although the description herein is focused on the application of positive airway pressure devices, especially for the treatment of sleep disordered breathing, there are many other applications for this technology. Other applications where this technology is of clear use include ventilators, nebulizers, oxygen delivery systems, and other respiratory applications where humidification is advantageous.

Hose is a term common to the respiratory applications described herein, but it should be understood that other similar terms such as conduit, passageway, channel, tube and air path can also be used.

The terms water, fluid, and vapor are used herein, and it should be understood to include any fluid suitable for humidification in respiratory applications, including fluids with added elements for comfort or therapeutic purposes. Terms such as gas, gaseous, vapor, droplet, mist, aerosolized fluid are all meant to indicate fluids converted into an inhalable humidified form.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A positive airway pressure system comprising:

an air flow generator configured to supply pressurized air to a patient interface via a lumen of an air conduit; and a humidifier comprising:

an air flow structure including an inner surface defining a lumen, the air flow structure configured to integrate the humidifier in-line with the air conduit such that the lumen of the air conduit and the lumen of the air flow structure form an air flow path for the pressurized air between the air flow generator and the patient interface, a humidification chamber configured to receive water from a water reservoir, and a humidification element configured to transform water in the humidification chamber into vapor that is added to the pressurized air via an aperture in the inner surface of the air flow structure, wherein a concave condensation channel is disposed in a portion of the inner surface of the air flow structure circumferentially around the aperture, the concave condensation channel is configured to return excess moisture from within the lumen of the air flow structure to the humidification element via the aperture.

2. The system of claim 1, wherein the humidifier further comprises a condensate collection element lining the portion of the inner surface of the air flow structure, the condensate collection element is configured to collect the excess moisture in the lumen of the airflow structure.

3. The system of claim 1, further comprising a sanitization chamber configured to sanitize water received from the water reservoir.

4. The system of claim 3, wherein the sanitization chamber includes an ultraviolet light source configured to sanitize the water provided to the humidification chamber.

5. The system of claim 1, wherein the humidifier further comprises a pump configured to pull water from the water reservoir into the humidifier.

6. The system of claim 5, wherein the humidifier further comprises a sensor disposed in the humidification chamber and configured to measure a water level of the water in the humidification chamber.

7. The system of claim 6, wherein the system is configured to apply measurements from the sensor to control the pump to maintain a predetermined water level in the humidification chamber.

8. The system of claim 1, wherein the humidifier further comprises a heating element configured to heat water entering the humidification chamber.

9. The system of claim 1, wherein the air flow structure comprises an inlet and an outlet, the lumen extending between the inlet and the outlet, the inlet and the outlet configured to integrate the humidifier in-line with the air conduit, wherein the vapor created by the humidification element is input into the lumen of the air flow structure.

10. The system of claim 9, wherein the humidifier further comprises a housing formed on an exterior surface of the air flow structure, wherein the humidification element and humidification chamber are disposed in the housing.

11. The system of claim 10, wherein the inlet of the air flow structure is coupled to the air flow generator, the outlet of the air flow structure is coupled to a first end of the air conduit, and a second end of the air conduit is coupled to the patient interface.

12. The system of claim 10, wherein a first end of the air conduit is coupled to the air flow generator, a second end of the air conduit is coupled to the inlet of the air flow structure, and the outlet of the air flow structure is coupled to the patient interface.

13. The system of claim 10, wherein a first section of the air conduit is coupled to the air flow generator, a second section of the air conduit is coupled to the patient interface, the inlet of the air flow structure is coupled to the first section of the air conduit, and the outlet of the air flow structure is coupled to the second section of the air conduit.

14. The system of claim 1, wherein the humidifier further comprises a port configured to fluidly couple with the water reservoir.

15. The system of claim 1, wherein the water reservoir is external to the humidifier and has a water storage capacity greater than a water storage capacity of the humidification chamber of the humidifier.

16. The system of claim 1, further comprising a controller configured to activate and de-activate the humidification element.

17. The system of claim 16, wherein the controller is further configured to activate and de-activate the humidification element in synchrony with inspiratory and expiratory phases of a user's breathing.

18. The system of claim 1, wherein the humidification element comprises an ultrasonic transducer configured to atomize water from the humidification chamber.

19. The system of claim 18, wherein the ultrasonic transducer comprises a piezoelectric material that oscillates at ultrasonic frequencies.

20. The system of claim 1, wherein the humidification element comprises a jet nebulizer.

21. The system of claim 1, wherein the concave condensation channel comprises a top and a bottom and a first circumference at the top and a second circumference at the bottom, wherein the first circumference is larger than the second circumference and the second circumference defines the aperture in the inner surface of the air flow structure.

22. A humidifier comprising:
an air flow structure including an inlet and an outlet and an inner surface defining a lumen, the lumen extending between the inlet and the outlet, the inlet and the outlet configured to integrate the humidifier in-line with an air conduit of a positive airway pressure system such that the lumen of the air flow structure and a lumen of the air conduit form an air flow path for pressurized air between an air flow generator and a patient interface of the positive airway pressure system;
a humidification chamber configured to receive water from a water reservoir; and
a humidification element configured to transform water in the humidification chamber into vapor that is added to the pressurized air via an aperture in the inner surface of the air flow structure,
wherein a concave condensation channel is disposed in a portion of the inner surface of the air flow structure circumferentially around the aperture, the concave condensation channel is configured to return excess moisture from within the lumen of the air flow structure to the humidification element via the aperture.

23. A humidifier comprising:
an air flow structure including an inlet and an outlet and an inner surface defining a lumen, the lumen extending between the inlet and the outlet, the inlet and the outlet configured to integrate the humidifier in-line with an air conduit of a positive airway pressure system such that the lumen of the air flow structure and a lumen of the air conduit form an air flow path for pressurized air between an air flow generator and a patient interface of the positive airway pressure system;
a humidification chamber configured to receive water from a water reservoir;
a humidification element configured to transform water in the humidification chamber into vapor that is added to the pressurized air; and
a condensate collection element lining a portion of the inner surface of the air flow structure, the condensate collection element is configured to collect excess moisture in the lumen of the airflow structure,
wherein a concave condensation channel is disposed in the portion of the inner surface of the air flow structure, the concave condensation channel is configured to return excess moisture from within the lumen of the air flow structure to the humidification element.

* * * * *